United States Patent
Matsumoto et al.

(10) Patent No.: US 10,584,363 B2
(45) Date of Patent: Mar. 10, 2020

(54) METHODS OF PRODUCING AND USING SINGLE-STRANDED DEOXYRIBONUCLEIC ACIDS AND COMPOSITIONS FOR USE IN PRACTICING THE SAME

(71) Applicant: Takara Bio USA, Inc., Mountain View, CA (US)

(72) Inventors: Hiroyuki Matsumoto, Mountain View, CA (US); Michael Haugwitz, Belmont, CA (US); Andrew Farmer, Los Altos, CA (US); Magnolia Bostick, San Mateo, CA (US)

(73) Assignee: Takara Bio USA, Inc., Mountain View, CA (US)

( * ) Notice: Subject to any disclaimer, the term of this patent is extended or adjusted under 35 U.S.C. 154(b) by 0 days.

(21) Appl. No.: 15/612,217

(22) Filed: Jun. 2, 2017

(65) Prior Publication Data

US 2017/0349927 A1 Dec. 7, 2017

Related U.S. Application Data

(60) Provisional application No. 62/345,615, filed on Jun. 3, 2016.

(51) Int. Cl.
| | | |
|---|---|---|
| *C12P 19/34* | (2006.01) | |
| *C12Q 1/6876* | (2018.01) | |
| *C12N 15/90* | (2006.01) | |
| *C12Q 1/6806* | (2018.01) | |
| *C12N 15/66* | (2006.01) | |
| *C12N 15/10* | (2006.01) | |

(52) U.S. Cl.
CPC ............. *C12P 19/34* (2013.01); *C12N 15/10* (2013.01); *C12N 15/66* (2013.01); *C12N 15/907* (2013.01); *C12Q 1/6806* (2013.01); *C12Q 1/6876* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 4,683,202 A * | 7/1987 | Mullis .................... | B01L 7/52 435/317.1 |
| 6,271,360 B1 | 8/2001 | Metz et al. | |
| 6,479,292 B1 | 11/2002 | Metz et al. | |
| 6,528,313 B1 | 3/2003 | Le Mouellic et al. | |
| 6,528,314 B1 | 3/2003 | Le Mouellic et al. | |
| 6,638,768 B1 | 10/2003 | Le Mouellic et al. | |
| 7,060,500 B2 | 6/2006 | Metz et al. | |
| 7,972,856 B2 | 7/2011 | Russell et al. | |
| 8,367,334 B2 | 2/2013 | Pugh et al. | |
| 8,535,886 B2 * | 9/2013 | Patel ...................... | C12N 15/10 435/6.1 |
| 8,846,387 B2 | 9/2014 | Russell et al. | |
| 2006/0068406 A1 * | 3/2006 | Affholter ............ | C12N 15/1013 435/6.13 |
| 2007/0178482 A1 | 8/2007 | Lezhava et al. | |
| 2008/0194029 A1 | 8/2008 | Hegemann et al. | |
| 2012/0276537 A1 | 11/2012 | Kühn et al. | |
| 2014/0304847 A1 | 10/2014 | Kühn et al. | |

FOREIGN PATENT DOCUMENTS

| | | |
|---|---|---|
| EP | 0253193 B1 | 10/1992 |
| EP | 0682112 B1 | 4/2007 |
| EP | 0682111 B1 | 10/2011 |
| EP | 1826215 B1 | 2/2012 |
| WO | WO 90/11354 A1 | 4/1990 |
| WO | WO 90/14092 A1 | 11/1990 |
| WO | WO 98/48005 A1 | 10/1998 |
| WO | WO 00/24917 A1 | 5/2000 |
| WO | WO 01/15740 A1 | 3/2001 |
| WO | WO 2005/108586 A1 | 11/2005 |
| WO | WO 2011/051390 A1 | 5/2011 |
| WO | WO 2012/168307 A2 | 12/2012 |

OTHER PUBLICATIONS

Molecular Biology Reagents/Protocols 1992, United States Biochemical Corporation, 1991, Cleveland, Ohio (pp. 101-104).*
Null et al, Rapid Communications in Mass Spectrometry 17: 2699 (2003).*
Banga et al. "Oligonucleotide-directed site-specific mutagenesis in *Drosophila melanogaster*," PNAS, vol. 89, Mar. 1992, pp. 1735-1739.
Bedell et al. "In vivo Genome Editing Using High Efficiency TALEN System," Nature, vol. 491, No. 7422, Nov. 1, 2012, pp. 114-118.
Campbell et al. "Homologous recombination involving small single-stranded oligonucleotides in human cells," The New Biologist, Nov. 1989, vol. 1, No. 2, pp. 223-227. (Abstract only).
Chang et al. "Genome editing with RNA-guided Cas9 nuclease in Zebrafish embryos," Cell Research, vol. 23, 2013, pp. 465-472.
Higuchi et al. "Production of single-stranded DNA templates by exonuclease digestion following the polymerase chain reaction," Nucleic Acids Research, vol. 17, No. 14, Jul. 25, 1989, pp. 5865.

(Continued)

*Primary Examiner* — James Martinell

(74) *Attorney, Agent, or Firm* — Bret E. Field; Bozicevic, Field & Francis LLP

(57) ABSTRACT

Methods of producing single-stranded deoxyribonucleic acids (ssDNAs) are provided. Aspects of the methods include generating a double stranded deoxyribonucleic acid (dsDNA) and then selectively degrading one strand of the dsDNA to produce a ssDNA. ssDNAs produced using methods of the invention find use in a variety of applications, including genomic modification applications. Also provided are compositions, e.g., kits, that find use in practicing various embodiments of the invention.

32 Claims, 14 Drawing Sheets

Specification includes a Sequence Listing.

(56) References Cited

OTHER PUBLICATIONS

Ho Sung Rhee et al. "Comprehensive Genome-wide Protein-DNA Interactions Detected at Single-Nucleotide Resolution," Cell, vol. 147, Dec. 9, 2011, pp. 1408-1419.
Krishnakumar et al. "A comprehensive assay for targeted multiplex amplification of human DNA sequences," PNAS, vol. 105, No. 27, Jul. 8, 2008, pp. 9296-9301.
Mandecki, W. "Oligonucleotide-directed double-strand break repair in plasmids of *Escherichia coli*: A method for site-specific mutagenesis," PNAS, vol. 83, Oct. 1986, pp. 7177-7181.
Miura et al. "CRISPR/Cas9-based generation of knockdown mice by intronic insertion of artificial microRNA using longer single-stranded DNA," Scientific Reports, vol. 5, Aug. 5, 2015, 12799, 11 pages.
Moerschell et al. "Transformation of yeast with synthetic oligonucleotides," PNAS, vol. 85, Jan. 1988, pp. 524-528.
Perkins et al. "Sequence-Dependent Pausing of Single Lambda Exonuclease Molecules," Science, vol. 301, Aug. 28, 2003, pp. 1914-1918.
Prediger, E. "Oligonucleotide modifications that block nuclease degradation," Integrated DNA Technologies, Decoded Newsletter, 2014, 2 pages. Retrieved from the Internet on Sep. 1, 2017, URL: https://www.ldtdna.com/pages/decoded/decoded-articles/core-concepts/decoded/2014/01/14/modification-highlight-modifications-that-block-nuclease-degradation.
Radecke et al. "Targeted Chromosomal Gene Modification in Human Cells by Single-Stranded Oligodeoxynucleotides in the Presence of a DNA Double-Strand Break," Molecular Therapy, vol. 14, No. 6, Dec. 2006, pp. 798-808.
Radecke et al. "Zinc-finger Nuclease-induced Gene Repair With Oligodeoxynucleotides: Wanted and Unwanted Target Locus Modifications," Molecular Therapy, vol. 18, No. 4, Apr. 2010, pp. 743-753.
Richardson et al. "Enhancing homology-directed genome editing by catalytically active and inactive CRISPR-Cas9 using asymmetric donor DNA," Nature Biotechnology, Advance Online Publication, Jan. 20, 2016, pp. 1-6.
Rudin et al. "Efficient Repair of HO-Induced Chromosomal Breaks in *Saccharomyces cerevisiae* by Recombination between Flanking Homologous Sequences," Molecular and Cellular Biology, vol. 8, No. 9, Sep. 1988, pp. 3918-3928.
Storici et al. "Chromosomal site-specific double-strand breaks are efficiently targeted for repair by oligonucleotides in yeast," PNAS, Dec. 9, 2003, vol. 100, No. 25, pp. 14994-14999.

\* cited by examiner hiPSCs with ssDNA donors (Day 9, sorting)

GAPDH
AcGFP1(S)

0% / ---

AAVS1
EF1a-AcGFP1(300-b arm)

3.19% / 1261

AAVS1
EF1a-AcGFP1(600-b arm)

```
                        SEQUENCE LISTING

<160> NUMBER OF SEQ ID NOS: 2

<210> SEQ ID NO 1
<211> LENGTH: 12
<212> TYPE: DNA
<213> ORGANISM: Artificial Sequence
<220> FEATURE:
<223> OTHER INFORMATION: Synthetic nucleotide

<400> SEQUENCE: 1
gggcggcgac ct                                                         12

<210> SEQ ID NO 2
<211> LENGTH: 12
<212> TYPE: DNA
<213> ORGANISM: Artificial sequence
<220> FEATURE:
<223> OTHER INFORMATION: Synthetic nucleotide

<400> SEQUENCE: 2
gggcggcgac ct                                                         12
```

METHODS OF PRODUCING AND USING SINGLE-STRANDED DEOXYRIBONUCLEIC ACIDS AND COMPOSITIONS FOR USE IN PRACTICING THE SAME

CROSS-REFERENCE TO RELATED APPLICATION

Pursuant to 35 U.S.C. § 119 (e), this application claims priority to the filing date of the U.S. Provisional Patent Application Ser. No. 62/345,615, filed Jun. 3, 2016; the disclosure of which application is herein incorporated by reference.

INTRODUCTION

Synthetic nucleic acid molecules have proven to be powerful tools useful in many settings including biomedical research, biotechnology, agriculture, industrial applications and clinical medicine. Single-stranded DNA (ssDNA), a single polymer strand of the normally bi-polymer strand of double stranded (dsDNA), represents one such useful molecule. Short ssDNAs have various uses in molecular and biochemical research and are most commonly employed as oligonucleotide primers in polymerase chain reaction (PCR) applications for both the detection of target nucleic acid sequences and production of nucleic acid molecules useful in downstream processes. Both short and long ssDNA oligomers find use as probes for microarray and in situ hybridization studies. Although many antisense technologies are RNA based, modified DNA antisense oligonucleotides have also been used in biomedical research applications to block complementary sense DNA targets from being expressed or direct the degradation of coding and non-coding RNAs by RNase H mediated mechanisms. Thus, ssDNA antisense oligonucleotides also allow the manipulation of gene function. ssDNA molecules of various lengths have also proved useful in providing replacement sequences for genomic recombination in genetic engineering. In the biotechnology arena, nucleic acid sequencing-by-synthesis technologies make use of ssDNA templates such as those employed in pyrosequencing.

Methods have been established for custom oligonucleotide chemical synthesis which allow researchers to design and order synthetic single-stranded oligos of desired sequences. These methods generally produce relatively short fragments of nucleic acids by solid-phase synthesis using phosphoramidite-modified nucleoside analogs having added protective groups. The nucleoside analogs are sequentially coupled in a defined order to produce a custom oligonucleotide. Chemical synthesis remains a viable option in many research applications and a method widely used by custom oligonucleotide manufacturers. An alternative approach involves biochemical production, e.g., utilizing enzymatic amplification of nucleic acid sequences rather than chemical synthesis. This biochemical approach may be exploited provided a nucleic acid template having the desired sequence is first synthesized or generated recombinantly. Biochemical production of desired nucleic acid molecules, including single and double stranded DNA, is frequently utilized by researchers; however, custom oligonucleotide producers predominantly favor chemical synthesis.

SUMMARY

Methods of producing and using single-stranded deoxyribonucleic acids (ssDNAs) are provided. Aspects of the methods include generating a double stranded deoxyribonucleic acid (dsDNA) and then selectively degrading one strand of the dsDNA to produce a ssDNA. ssDNAs produced using methods of the invention find use in a variety of applications, including genomic modification applications. Also provided are compositions, e.g., kits, that find use in practicing various embodiments of the invention.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DEFINITIONS

Figure 1:
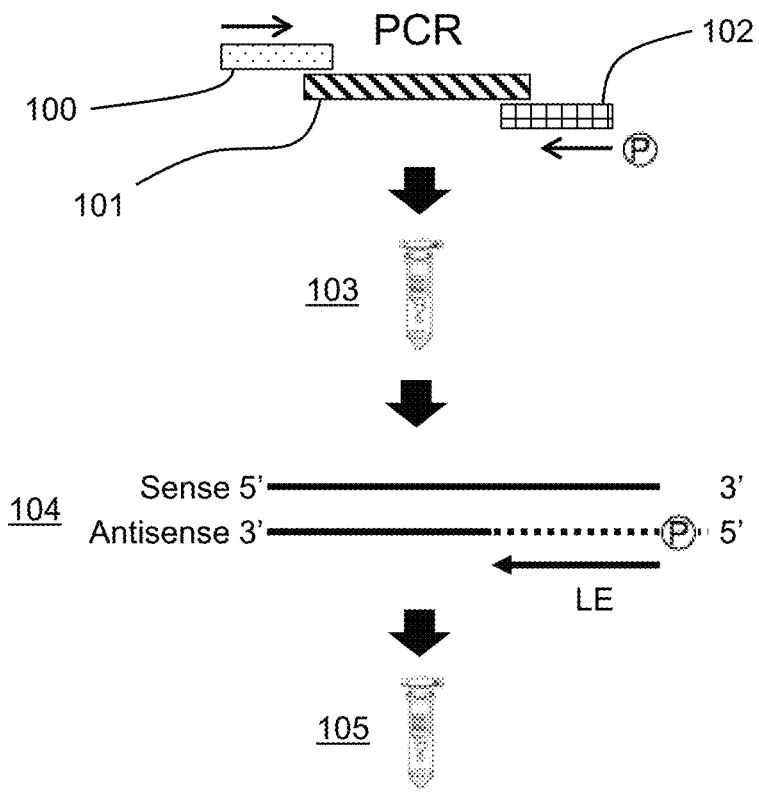
FIG. 1 depicts a schematic representation of a procedure for the generation of a dsDNA and subsequent strand-selective degradation to produce a ssDNA according to certain embodiments as describe herein.

Unless defined otherwise, all technical and scientific terms used herein have the same meaning as commonly understood by one of ordinary skill in the art to which this invention belongs. Still, certain elements are defined below for the sake of clarity and ease of reference.

The terms "nucleic acid", "polynucleotide" and "oligonucleotide" are used interchangeably herein to include a polymeric form of nucleotides, either ribonucleotides or deoxyribonucleotides. This term refers only to the primary structure of the molecule. Thus, the terms include triple-, double- and single-stranded DNA, as well as triple-, double- and single-stranded RNA, except where specifically designated otherwise. The terms also include such molecules with modifications, such as by methylation and/or by capping, and unmodified forms of a polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing non-nucleotidic backbones, polymers, and other synthetic sequence-specific nucleic acid polymers providing that the polymers contain nucleobases in a configuration which allows for base pairing and base stacking, such as is found in DNA and RNA. Polynucleotides also encompass those containing one or more "nucleoside analogs" or "nucleotide analogs", which are nucleoside or nucleotide analogs of naturally occurring nucleosides and nucleotides as in e.g., RNA and DNA.

Non-limiting examples of nucleoside analogs and reagents used in the synthesis or modification of nucleoside analogs include but are not limited to e.g., 1,3,9-Trimethylxanthine; 1,3-Dimethyluric acid; 1,N6-Etheno-2'-deoxyadenosine; 1,N6-Ethenoadenine; 1-Allyl-3,7-dimethyl-8-phenylxanthine; 1-Allyl-3,7-dimethyl-8-sulfophenylxanthine; 1-Cyclohexyluracil; 1-Methylthymine; 1-Methyluric acid; 2,3'-Anhydrothymidine; 2',3',5'-Tri-O-acetyladenosine; 2',3',5'-Tri-O-acetylcytidine hydrochloride; 2',3',5'-Tri-O-acetyluridine; 2',3',5'-Tri-O-benzoyluridine; 2',3'-Dideoxy-5-iodouridine; 2',3'-Dideoxyadenosine; 2',3'-Di-O-benzoyluridine; 2',3'-O-Isopropylidene-6-mercaptopurine riboside; 2',3'-O-Isopropylideneguanosine; 2',3'-O-lsopropylideneuridine; 2'-Deoxyadenosine monohydrate; 2'-Deoxycytidine; 2'-Deoxycytidylyl(3'→5')-2'-deoxyguanosine; 2'-Deoxyguanosine monohydrate; 2'-Deoxyinosine; 2'-Deoxyuridine; 2'-O-Methyladenosine; 2'-O-Methylcytidine; 2-Amino-6-chloropurine riboside; 2-Amino-6-methylmercaptopurine; 2-Aminopurine; 2-Chloro-2'-deoxyadenosine antileukemic; 2-Chloro-N6-cyclopentyladenosine adenosine receptor agonist; 2-Dimethylamino-6-hydroxypurine; 2-Mercaptopurine; 2-Thiouracil; 3'-Deoxyguanosine; 3'-O-Methyluridine; 3-Methyladenine; 3-Methyluracil; 4,5,6-Triaminopyrimidine sulfate; 4-Amino-1,3-dimethyl-2,6-dioxy-5-nitrosopyrimidine; 4-Amino-5-carboxy-2-ethylmercaptopyrimidine; 4-Chlorouracil; 4-Methylumbelliferyl β-L-fucoside glycosidase substrate; 4-Thiouridine; 5,6-Dihydrodeoxyuridine; 5'-(4-Fluorosulfonylbenzoyl)adenosine hydrochloride; 5'-Amino-5'-deoxythymidine; 5'-Deoxy-5'-(methylthio)adenosine; 5'-Deoxyadenosine methylthioadenosine/S-adenosylhomocysteine (MTA/SAH) nucleosidase substrate; 5'-O-(4,4'-Dimethoxytrityl)-2'-deoxyuridine; 5'-O-Tritylthymidine; 5-Carbethoxyuracil; 5-Carboxy-2-thiouracil; 5-Chloro-2'-deoxyuridine thymidine analog; 5-Ethyl-2'-deoxyuridine; 5-Fluoro-1-(tetrahydro-2-furyl)uracil; 5-Fluorouridine; 5-lodo-2,4-dimethoxy-pyrimi-dine; 5-lodo-2'-deoxycytidine; 5-lodocytosine; 5-Methoxyuridine; 5-Methyl-2-thiouridine; 5-Methylcytidine; 5-Methylcytosine hydrochloride; 5-Methyluridine; 5-n-Propyluracil; 5-Propyl-2-thiouracil; 5-Sulfaminouracil; 6-(Dimethylamino)purine; 6-Azauracil; 6-Azauridine; 6-Chloropurine riboside; 6-Cyanopurine; 6-Ethoxypurine; 6-Ethylmercaptopurine; 6-Mercaptopurine-2'-deoxyriboside; 6-Methylmercaptopurine riboside; 6-Methylpurine; 6-n-Butoxypurine; 6-n-Heptylmercaptopurine crystalline; 6-n-Propoxypurine; 6-Phenyl-2-thiouracil; 6-Propyl-2-thiouracil; 6-Selenopurine; 7-Methylguanosine; 8-(3-Carboxypropyl)-1,3-dimethylxanthine; 8-Bromo-2',3',5'-tri-O-acetylguanosine; 8-Bromoadenosine; 9-(2',3',5'-Tri-O-benzyl-β-D-arabinofuranosyl)adenine; 9-Ethylguanine; 9-Methyluric acid; Adefovir dipivoxil; Allopurinol riboside; Bromonucleic acid; Glycitein; Guanosine; Guanylyl(2'→5') adenosine; Guanylyl(3'→5')cytidine; Guanylyl(3'→5')uridine; Hypoxanthine; Indoxyl β-D-glucoside; Isocytosine; lsoxanthopterin; Kinetin riboside; N2-Isobutyryl-3'-O-benzoyl-2'-deoxyguanosine; N2-Isobutyryl-5'-O-(4,4'-dimethoxytrityl)-2'-deoxyguanosine; N2-Isobutyryl-5'-O-(4,4'-dimethoxytrityl)-2'-deoxyguanosine 3'-O-succinic acid; N2-Methylguanosine; N4-Acetylcytidine; N4-Aminocytidine; N4-Anisoylcytidine; N4-Benzoyl-5'-O-(4,4'-dimethoxytrityl)-2'-deoxycytidine; N4-Octadecylcytosine β-D-arabinofuranoside; N6-Benzoyladenine; N6-Methyl-2'-deoxyadenosine; N6-Phenoxyacetyl-5'-O-(4,4'-dimethoxytrityl)-2'-deoxyadenosine; Orotic acid potassium salt; Orotidine; Oxypurinol; R(–)-PD 128,908 hydrochloride; S-(2-Hydroxy-5-nitrobenzyl)-6-thioguanosine; S-(2-Hydroxy-5-nitrobenzyl)-6-thioinosine; Se-(p-Nitrobenzyl)-6-selenoinosine; Thymidylyl(3'→5')-2'-deoxyadenosine; Thymidylyl(3'→5')thymidine; Thymine 1-β-D-arabinofuranoside; Trifluorothymidine; Uracil 1-β-D-arabinofuranoside; Zeatin riboside; and the like.

The term "primer" as used herein, refers to an oligonucleotide which acts to initiate synthesis of a complementary nucleic acid strand when placed under conditions in which synthesis of a primer extension product is induced, e.g., in the presence of nucleotides and a polymerization-inducing agent such as a DNA or RNA polymerase and at suitable temperature, pH, metal concentration, and salt concentration. Primers are generally of a length compatible with their use in synthesis of primer extension products, and may be in a range from 6 bp to 150 bp or more, including but not limited to e.g., 6 bp to 150 bp, 7 bp to 150 bp, 8 bp to 150 bp, 9 bp to 150 bp, 10 bp to 150 bp, 11 bp to 150 bp, 12 bp to 150 bp, 13 bp to 150 bp, 14 bp to 150 bp, 15 bp to 150 bp, 16 bp to 150 bp, 17 bp to 150 bp, 18 bp to 150 bp, 19 bp to 150 bp, 20 bp to 150 bp, 25 bp to 150 bp, 30 bp to 150 bp, 35 bp to 150 bp, 40 bp to 150 bp, 6 bp to 100 bp, 7 bp to 100 bp, 8 bp to 100 bp, 9 bp to 100 bp, 10 bp to 100 bp, 11 bp to 100 bp, 12 bp to 100 bp, 13 bp to 100 bp, 14 bp to 100 bp, 15 bp to 100 bp, 16 bp to 100 bp, 17 bp to 100 bp, 18 bp to 100 bp, 19 bp to 100 bp, 20 bp to 100 bp, 25 bp to 100 bp, 30 bp to 100 bp, 35 bp to 100 bp, 40 bp to 100 bp, 6 bp to 40 bp, 7 bp to 40 bp, 8 bp to 40 bp, 9 bp to 40 bp, 10 bp to 40 bp, 11 bp to 40 bp, 12 bp to 40 bp, 13 bp to 40 bp, 14 bp to 40 bp, 15 bp to 40 bp, 16 bp to 40 bp, 17 bp to 40 bp, 18 bp to 40 bp, 19 bp to 40 bp, 20 bp to 40 bp, 25 bp to 40 bp, 30 bp to 40 bp, 35 bp to 40 bp, 6 bp to 20 bp, 7 bp to 20 bp, 8 bp to 20 bp, 9 bp to 20 bp, 10 bp to 20 bp, 11 bp to 20 bp, 12 bp to 20 bp, 13 bp to 20 bp, 14 bp to 20 bp, 15 bp to 20 bp, 16 bp to 20 bp, 17 bp to 20 bp, 18 bp to 20 bp, and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length. Primer lengths as described herein may include only the portion of the primer that hybridizes to its complementary template and may exclude, e.g., portions that are not complementary to a template including but not limited to e.g., homology arms that may not be complementary to a template.

DETAILED DESCRIPTION

Methods of producing single-stranded deoxyribonucleic acids (ssDNAs) are provided. Aspects of the methods include generating a double stranded deoxyribonucleic acid (dsDNA) and then selectively degrading one strand of the dsDNA to produce a ssDNA. ssDNAs produced using methods of the invention find use in a variety of applications, including genomic modification applications. Also provided are compositions, e.g., kits, that find use in practicing various embodiments of the invention.

Before the present methods are described, it is to be understood that this invention is not limited to particular method described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a nucleic acid" includes a plurality of such nucleic acids and reference to "the enzyme" includes reference to one or more enzymes and equivalents thereof.

The publications discussed herein are provided solely for their disclosure prior to the filing date of the present disclosure. Nothing herein is to be construed as an admission that the present invention is not entitled to antedate such publication by virtue of prior invention. Further, the dates of publication provided may be different from the actual publication dates which may need to be independently confirmed.

Methods

As summarized above, aspects of the disclosure include methods of producing and using single-stranded nucleic acids. Single-stranded nucleic acids are mono-chain polymers of nucleoside blocks, where nucleosides include but are not limited to N-glycosides of ribose and deoxyribose and derivatives thereof. Accordingly, single-stranded nucleic acids include single-chain or single-stranded DNA (ssDNA) polymers of the more commonly found double-stranded DNA (dsDNA), single-stranded RNA (ssRNA) and modified variants thereof. Additionally, single-stranded nucleic acids include those nucleic acid polymers containing various combinations of nucleosides including only naturally occurring nucleosides, only synthetic nucleoside analogs, and combinations of both naturally occurring nucleosides and synthetic nucleoside analogs.

ssDNAs, e.g., as produced according to and/or employed in the methods described herein, will vary in length where the length of a ssDNA may range from 20 bp or less to 10 kb or more up to a megabase, including but not limited to e.g., 20 bp to 10 kb, 20 bp to 9 kb, 20 bp to 8 kb, 20 bp to 7 kb, 20 bp to 6 kb, 20 bp to 5 kb, 20 bp to 4.5 kb, 20 bp to 4 kb, 20 bp to 3.5 kb, 20 bp to 3 kb, 20 bp to 2.5 kb, 20 bp to 2 kb, 20 bp to 1.5 kb, 20 bp to 1 kb, 20 bp to 900 bp, 20 bp to 800 bp, 20 bp to 700 bp, 20 bp to 600 bp, 20 bp to 500 bp, 20 bp to 400 bp, 20 bp to 300 bp, 20 bp to 200 bp, 20 bp to 150 bp, 20 bp to 100 bp, 20 bp to 50 bp, 50 bp to 10 kb, 100 bp to 10 kb, 150 bp to 10 kb, 200 bp to 10 kb, 300 bp to 10 kb, 400 bp to 10 kb, 500 bp to 10 kb, 600 bp to 10 kb, 700 bp to 10 kb, 800 bp to 10 kb, 900 bp to 10 kb, 1 kb to 10 kb, 1.5 kb to 10 kb, 2 kb to 10 kb, 2.5 kb to 10 kb, 3 kb to 10 kb, 3.5 kb to 10 kb, 4 kb to 10 kb, 4.5 kb to 10 kb, 5 kb to 10 kb, 200 bp to 10 kb, 200 bp to 9 kb, 200 bp to 8 kb, 200 bp to 7 kb, 200 bp to 6 kb, 200 bp to 5 kb, 200 bp to 4.5 kb, 200 bp to 4 kb, 200 bp to 3.5 kb, 200 bp to 3 kb, 200 bp to 2.5 kb, 200 bp to 2 kb, 200 bp to 1.5 kb, 200 bp to 1 kb, 300 bp to 10 kb, 300 bp to 9 kb, 300 bp to 8 kb, 300 bp to 7 kb, 300 bp to 6 kb, 300 bp to 5 kb, 300 bp to 4.5 kb, 300 bp to 4 kb, 300 bp to 3.5 kb, 300 bp to 3 kb, 300 bp to 2.5 kb, 300 bp to 2 kb, 300 bp to 1.5 kb, 300 bp to 1 kb, 400 bp to 10 kb, 400 bp to 9 kb, 400 bp to 8 kb, 400 bp to 7 kb, 400 bp to 6 kb, 400 bp to 5 kb, 400 bp to 4.5 kb, 400 bp to 4 kb, 400 bp to 3.5 kb, 400 bp to 3 kb, 400 bp to 2.5 kb, 400 bp to 2 kb, 400 bp to 1.5 kb, 400 bp to 1 kb, 500 bp to 10 kb, 500 bp to 9 kb, 500 bp to 8 kb, 500 bp to 7 kb, 500 bp to 6 kb, 500 bp to 5 kb, 500 bp to 4.5 kb, 500 bp to 4 kb, 500 bp to 3.5 kb, 500 bp to 3 kb, 500 bp to 2.5 kb, 500 bp to 2 kb, 500 bp to 1.5 kb, 500 bp to 1 kb, etc.

In some instances, a ssDNA, e.g., as produced according to and/or employed in the methods described herein, may be a long ssDNA. The term "long ssDNA" as used herein refers to ssDNAs of varying length but generally including e.g., those lengths of ssDNA not readily or efficiently or cost-effectively generated by conventional oligonucleotide chemical synthesis. As used herein the term "long", as it refers to ssDNA molecules, will generally include those ssDNAs of at least 150 bp or more in length, including but not limited to e.g., 200 bp or longer, 250 bp or longer 300 bp or longer, 350 bp or longer, 400 bp or longer, 450 bp or longer, 500 bp or longer, etc.

Production of Single-Stranded Nucleic Acids Via Selective Strand Degradation

In some instances, methods of generating single-stranded nucleic acids as described herein include the production of double-stranded nucleic acids having two structurally different strands. Such structural differences between the two strands of a double-stranded nucleic acid may be utilized for the selective degradation of one strand to produce a desired single-stranded nucleic acid. For simplicity, throughout the instant disclosure a double-stranded nucleic acid may be referred to generally as a double-stranded DNA (dsDNA). The general use of the term "dsDNA" throughout the disclosure should not be considered to limit the methods as described herein to those specifically involving dsDNA, but should instead be considered to broadly encompass other double-stranded nucleic acids where appropriate, including but not limited to e.g., double-stranded RNA (dsRNA) and synthetic analogs thereof, double-stranded DNA/RNA hybrids, and double-stranded nucleic acids containing one or more modified nucleosides/nucleotides and/or nucleoside/nucleotide analogs. Accordingly, in some instances, methods of generating ssDNA as described herein include the production of dsDNA having two structurally different strands. Such structural differences between the two strands of a dsDNA may be utilized for the selective degradation of one strand of the dsDNA to produce a desired ssDNA.

The introduction of one or more structural differences into one strand of a dsDNA or the production of a dsDNA with structurally different strands may be achieved by a variety of methods including but not limited to e.g., polymerase chain reaction (PCR) methods, nucleic acid ligation methods, direct chemical synthesis methods, and the like.

PCR-based production of a dsDNA having structurally different strands will generally include, but does not necessarily require, incorporation of a structural modification into the dsDNA during amplification. The modification may be present on any suitable component of the PCR reaction for incorporation into the dsDNA during the amplification, including but not limited to e.g., a primer, a deoxynucleotide (dNTP), etc.

In some instances, a nucleotide analog or other synthetic dNTP may be incorporated into the growing nucleic acid during the amplification process. In other instances, a modified primer (e.g., modified sense primer, modified antisense primer) may be incorporated into the dsDNA during the amplification reaction. Suitable nucleotide analogs and modified primers include modified elements that, upon incorporation, provide structural differences to the dsDNA that differentially affects the ability to degrade one strand of the dsDNA versus the other. Such differences may be protective, meaning the difference protects one strand from degradation, or permissive, meaning that the difference allows a particular strand to be degraded.

Permissive and/or protective structural differences may be incorporated during a PCR reaction due to the presence of a permissive modification, a protective modification or a combination thereof on one or more PCR primers used during the amplification. For example, a suitable permissive end-modification and/or protective base modification, including e.g., those described herein, may be incorporated into a dsDNA when present on a primer of the PCR reaction. In some embodiments, a primer with an attached 5' phosphate may, during the PCR amplification, incorporate the 5'-phosphate into the produced dsDNA by incorporation of the primer into the dsDNA. In some instances, a suitable protective base modification, including e.g., those described herein, may be incorporated into a dsDNA when present on a primer of the PCR reaction. For example, a primer with an incorporated blocking base modification may, during the PCR amplification, incorporate the blocking base modification into the produced dsDNA by incorporation of the primer into the dsDNA.

In some instances, a primer containing two or more, e.g., 3 or more, 4 or more, 4 or more, 6 or more, 7 or more, 8 or more, 9 or more, 10 or more, etc. modifications (including where the modifications are the same or different) may be incorporated into a dsDNA during PCR amplification. For example, in some instances, a primer containing two or more, e.g., 3 or more, 4 or more, 4 or more, 6 or more, 7 or more, 8 or more, 9 or more, 10 or more, etc. protective base modifications (including where the protective base modifications are the same or different) may be incorporated into a dsDNA during PCR amplification. In other instances, two or more different modifications, e.g., a permissive end-modification (e.g., a 5'-phosphate modification) and one or more protective base modifications may be present on a primer that is incorporated into a dsDNA during PCR amplification to generate a dsDNA containing two or more different modifications.

In some instances, primers may be used in pairs (e.g., forward and reverse primer pairs) to incorporate two or more modifications into a dsDNA of the instant disclosure where each primer of the pair contains at least one modification. Accordingly, a primer pair (e.g., a forward and reverse primer pair) may collectively contain two or more, e.g., 3 or more, 4 or more, 5 or more, 6 or more, 7 or more, 8 or more, 9 or more, 10 or more, etc. modifications (including where the modifications are the same or different). In certain instances, one primer of the pair may contain a permissive moiety and the other primer may contain a protective moiety such that upon incorporation of the primers into the amplified dsDNA during a PCR the produced dsDNA will contain a first strand having the permissive moiety and a second strand having the protective moiety. The use of primer pairs is not limited to the introduction of protective and permissive moieties into separate strands as described but also includes e.g., where the primer pair introduces permissive moieties into both strands, including e.g., where the primer pair introduces permissive moieties into both strands but one or more protective moieties into only one strand.

Figure 15:
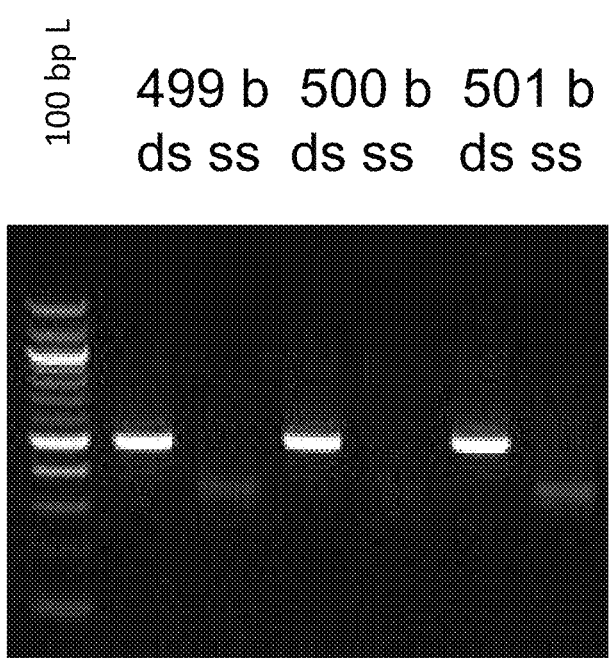
FIG. 15 depicts the verification of produced ssDNA and dsDNA fragments of depicted lengths.

Single-stranded DNA degradation can be, in some instances, affected by sequence context (See e.g., FIG. 15 and description below). In some instances, when an initial primer binding site results in reduced ssDNA formation, the primer binding site positions may be changed in order to promote efficient ssDNA formation. The primer binding sites may be shifted by 1, 2, 3, 4, 5, 6, 7, 8, 9 or 10 or more bases upstream or downstream of the initial primer binding site. In some instances, the primer binding sites may be shifted by at most 1, 2, 3, 4, 5, 6, 7, 8, 9, or 10 bases upstream or downstream of the initial primer binding site. In some instances, the primer binding site is shift by one nucleotide upstream or downstream of the initial primer binding site. In some embodiments, the methods of the disclosure provide for testing the optimal primer binding site position on the target nucleic acid.

In embodiments directed to the use of the produced ssDNA in homology-based recombination, as described in more detail below, primer pairs may contain sequence having homology to the sequence of a target integration site. As such, in some instances, primer pairs may contain sequence of "right" and "left" homology arms that each has homology to a portion of a target integration site. The length of such homology arms will vary and may range from 50 bp or less to 1 kb or more up to 2 kb and may range from e.g., 50 bp to 1 kb, 50 bp to 900 bp, 50 bp to 800 bp, 50 bp to 700 bp, 50 bp to 600 bp, 50 bp to 500 bp, 50 bp to 400 bp, 50 bp to 300 bp, 50 bp to 200 bp, 50 bp to 100 bp, 100 bp to 1 kb, 150 bp to 1 kb, 200 bp to 1 kb, 250 bp to 1 kb, 300 bp to 1 kb, 350 bp to 1 kb, 400 bp to 1 kb, 450 bp to 1 kb, 500 bp to 1 kb, 550 bp to 1 kb, 600 bp to 1 kb, 650 bp to 1 kb, 700 bp to 1 kb, 750 bp to 1 kb, 800 bp to 1 kb, 850 bp to 1 kb, 900 bp to 1 kb, 950 bp to 1 kb, 150 bp to 900 bp, 150 bp to 800, 150 bp to 700, 150 bp to 600, 200 bp to 900 bp, 200 bp to 800, 200 bp to 700, 200 bp to 600, 300 bp to 900 bp, 300 bp to 800, 300 bp to 700, 300 bp to 600, and the like. Depending on various factors including e.g., the type of PCR used, the PCR template configuration, etc. the PCR primers may or may not include sequence in addition to that of the homology arms.

Primers useful in the methods as described herein can vary in length depending on various factors including e.g., the particular PCR technique used, the desired end-use of the produced ssDNA (e.g., whether the primers are configured to be attached to the homology arms, etc.), etc. The length of primers, e.g., excluding any attached homology arms, may range from 6 bp to 150 bp or more, including but not limited to e.g., 6 bp to 150 bp, 7 bp to 150 bp, 8 bp to 150 bp, 9 bp to 150 bp, 10 bp to 150 bp, 11 bp to 150 bp, 12 bp to 150 bp, 13 bp to 150 bp, 14 bp to 150 bp, 15 bp to 150 bp, 16 bp to 150 bp, 17 bp to 150 bp, 18 bp to 150 bp, 19 bp to 150 bp, 20 bp to 150 bp, 25 bp to 150 bp, 30 bp to 150 bp, 35 bp to 150 bp, 40 bp to 150 bp, 6 bp to 100 bp, 7 bp to 100 bp, 8 bp to 100 bp, 9 bp to 100 bp, 10 bp to 100 bp, 11 bp to 100 bp, 12 bp to 100 bp, 13 bp to 100 bp, 14 bp to 100 bp, 15 bp to 100 bp, 16 bp to 100 bp, 17 bp to 100 bp, 18 bp to 100 bp, 19 bp to 100 bp, 20 bp to 100 bp, 25 bp to 100 bp, 30 bp to 100 bp, 35 bp to 100 bp, 40 bp to 100 bp, 6 bp to 40 bp, 7 bp to 40 bp, 8 bp to 40 bp, 9 bp to 40 bp, 10 bp to 40 bp, 11 bp to 40 bp, 12 bp to 40 bp, 13 bp to 40 bp, 14 bp to 40 bp, 15 bp to 40 bp, 16 bp to 40 bp, 17 bp to 40 bp, 18 bp to 40 bp, 19 bp to 40 bp, 20 bp to 40 bp, 25 bp to 40 bp, 30 bp to 40 bp, 35 bp to 40 bp, 6 bp to 20 bp, 7 bp to 20 bp, 8 bp to 20 bp, 9 bp to 20 bp, 10 bp to 20 bp, 11 bp to 20 bp, 12 bp to 20 bp, 13 bp to 20 bp, 14 bp to 20 bp, 15 bp to 20 bp, 16 bp to 20 bp, 17 bp to 20 bp, 18 bp to 20 bp, etc.

The length of fragments used to construct a linear double stranded DNA donor for homology-based recombination will vary and may range from, but are not limited to, 55 bp or less to 1 kb or more, including e.g., 55 bp to 1 kb, 55 bp to 900 bp, 55 bp to 800 bp, 55 bp to 700 bp, 55 bp to 600 bp, 55 bp to 500 bp, 55 bp to 400 bp, 55 bp to 300 bp, 55 bp to 200 bp, 55 bp to 100 bp, 65 bp to 1 kb, 65 bp to 900 bp, 65 bp to 800 bp, 65 bp to 700 bp, 65 bp to 600 bp, 65 bp to 500 bp, 65 bp to 400 bp, 65 bp to 300 bp, 65 bp to 200 bp, 65 bp to 100 bp, 75 bp to 1 kb, 75 bp to 900 bp, 75 bp to 800 bp, 75 bp to 700 bp, 75 bp to 600 bp, 75 bp to 500 bp, 75 bp to 400 bp, 75 bp to 300 bp, 75 bp to 200 bp, 75 bp to 100 bp, 85 bp to 1 kb, 85 bp to 900 bp, 85 bp to 800 bp, 85 bp to 700 bp, 85 bp to 600 bp, 85 bp to 500 bp, 85 bp to 400 bp, 85 bp to 300 bp, 85 bp to 200 bp, 85 bp to 100 bp, 95 bp to 1 kb, 95 bp to 900 bp, 95 bp to 800 bp, 95 bp to 700 bp, 95 bp to 600 bp, 95 bp to 500 bp, 95 bp to 400 bp, 95 bp to 300 bp, 95 bp to 200 bp, 95 bp to 100 bp, 100 bp to 1 kb, 150 bp to 1 kb, 200 bp to 1 kb, 250 bp to 1 kb, 300 bp to 1 kb, 350 bp to 1 kb, 400 bp to 1 kb, 450 bp to 1 kb, 500 bp to 1 kb, 550 bp to 1 kb, 600 bp to 1 kb, 650 bp to 1 kb, 700 bp to 1 kb, 750 bp to 1 kb, 800 bp to 1 kb, 850 bp to 1 kb, 900 bp to 1 kb, 950 bp to 1 kb, 150 bp to 900 bp, 150 bp to 800, 150 bp to 700, 150 bp to 600, 200 bp to 900 bp, 200 bp to 800, 200 bp to 700, 200 bp to 600, 300 bp to 900 bp, 300 bp to 800, 300 bp to 700, 300 bp to 600, etc.

dsDNA produced by PCR for use in the subject methods may include but is not limited to a dsDNA containing one or more permissive moieties on one strand, a dsDNA containing one or more protective moieties on one strand, a dsDNA containing both one or more permissive moieties on one strand and one or more protective moieties on the other strand, a dsDNA containing one or more permissive moieties on both strands and one or more protective moieties on one strand, etc. While the method is not so limited, incorporation of permissive moieties and/or protective moieties using PCR primers, due to the particular dynamics of PCR reactions, can result in the moieties being present on the ends or near the ends of the generated dsDNA. The presence of permissive moieties and/or protective moieties at the ends of the generated dsDNA promotes early interaction of the moieties with exonucleases of a degradation reaction. For example, when a protective moiety is incorporated into the 5' end of a dsDNA due to the presence of the protective moiety in a PCR primer, a 5' to 3' exonuclease having activity that is blocked by the protective moiety will be blocked upon interaction with the protective moiety in the primer sequence and thus will not proceed into non-primer sequence.

Any convenient method of PCR may find use in generating dsDNA of the instant disclosure including conventional PCR and various PCR variants. Conventional PCR generally includes the use of a pair of primers (i.e., forward and reverse), a dsDNA template and necessary reagents (e.g., dTNPs, polymerase, etc.). PCR variants useful in the subject methods include but are not limited to e.g., asymmetric PCR, nested PCR, Hot-start PCR, touchdown PCR, Assembly PCR (i.e. Polymerase Cycling Assembly), Overlap Extension PCR, Ligation-mediated PCR, RT-PCR, isothermal PCR, and the like.

Permissive and/or protective structural differences may be incorporated during a ligation reaction due to the presence of a permissive modification, a protective modification or a combination thereof on one or more DNA fragments used during the ligation. Ligation-based production of a dsDNA having structurally different strands will generally include, but does not necessarily require, ligation of two or more dsDNA segments where at least one of the dsDNA segments contains a permissive moiety, a protective moiety or a combination thereof. The term "dsDNA segment" as used herein generally refers to a DNA fragment that is at least partially double stranded, including but not limited to dsDNA fragments that are entirely double stranded, dsDNA fragments having one or more 3' overhangs, dsDNA fragments having one or more 5' overhangs, dsDNA fragments having one blunt end and one 3' overhang, dsDNA fragments having one blunt end and one 5' overhang and dsDNA fragments having one 3' overhang and one 5' overhang.

In some instances, the unligated ends of a particular dsDNA segment may serve as a permissive or protective moiety depending on the ability or inability of a particular exonuclease to degrade a strand of the dsDNA having such an end. For example, in some instances, an unligated blunt end may serve as a protective or permissive moiety depending on the ability or inability of a particular exonuclease to degrade the blunt end. In some instances, an unligated 5' overhang may serve as a protective or permissive moiety depending on the ability or inability of a particular exonuclease to degrade the 5' overhang. In some instances, an unligated 3' overhang may serve as a protective or permissive moiety depending on the ability or inability of a particular exonuclease to degrade the 3' overhang.

A dsDNA segment may include all or a portion of a coding sequence or may not contain any coding sequence. A dsDNA segment may include all or a portion of a non-coding sequence or may not contain any non-coding sequence.

In embodiments directed to the use of the produced ssDNA in homology-based recombination, as described in more detail below, a dsDNA segment as used in a ligation reaction may include a homology arm, e.g., a "right homology arm" or a "left homology arm", as described above. In some instances, a pair of dsDNA segments will include right and left homology arms, including where the right homology arm is present on a first dsDNA segment and the left homology arm is present on the second dsDNA segment. Pairs of dsDNA segments may be ligated to one another or each ligated to one or more intervening dsDNA segments.

dsDNA segments may be generated from one or more plasmids or other source of DNA sequence (including e.g., synthetically derived DNA sequence, DNA sequence obtained from an bacterial genome, DNA sequence obtained from an archaea genome, DNA sequence obtained from an eukaryotic genome, DNA obtained from a bacteriophage, DNA obtained from a virus, etc.) using various cloning methods including e.g., restriction digestion, PCR, rolling circle replication, etc. Alternatively, dsDNA segments of any desired sequence and of essentially any reasonable length may be custom ordered, e.g., as synthesized DNA "blocks" e.g., as available as "gBlocks" from Integrated DNA Technologies, Inc. (Coralville, Iowa). Where an initially generated or acquired dsDNA segment contains ends that are incompatible with downstream processes, the incompatible ends may be modified to be compatible, e.g., by generating "sticky-ends" (e.g., by partial exonuclease digestion, by restriction enzyme digestion, etc.), by "blunt-ending" (e.g., bp restriction enzyme digestion, by "end-filling" with a polymerase, etc.), and the like. In some instances, an initially generated dsDNA segment may be configured to contain one or more restriction enzyme recognition sequences for use in one or more restriction enzyme digestion reactions, e.g., to prepare one or more compatible ends.

In some instances, one or more dsDNA segments may be modified to contain one or more permissive motifs and/or one or more protective motifs, as described herein, prior to the ligation. For example, in some instances, a dsDNA is produced or modified to contain a 5' phosphate such that, upon ligation to one or more additional dsDNA segments, the 5' phosphate provides a permissive moiety for use in strand-selective degradation. In some instances, a dsDNA is produced or modified to contain a protective base modification such that, upon ligation to one or more additional dsDNA segments, the protective base modification provides a protective moiety for use in strand selective degradation.

Protective base modifications (including but not limited to e.g., phosphorothioate internucleotide linkages) may be present anywhere on or within a dsDNA segment, including but not limited to at the 3' or 5' end of the dsDNA segment, near the end of the dsDNA segment (e.g., within 50 bp or less, including e.g., 40 bp or less, 30 bp or less, 25 bp or less, 20 bp or less, 15 bp or less, 10 bp or less, etc., from the 3' or 5' end of the dsDNA segment) or within the dsDNA segment but not near an end (e.g., more than 10 bp, including e.g., more than 15 bp, more than 20 bp, more than 25 bp, more than 30 bp, more than 40 bp, more than 50 bp, etc., from the 3' or 5' end of the dsDNA segment), or any combination thereof.

In certain instances, a dsDNA segment containing two or more, e.g., 3 or more, 4 or more, 5 or more, 6 or more, 7 or more, 8 or more, 9 or more, 10 or more, etc. modifications (including where the modifications are the same or different) may be incorporated into a dsDNA during a ligation reaction. For example, in some instances, a dsDNA segment containing two or more, e.g., 3 or more, 4 or more, 5 or more, 6 or more, 7 or more, 8 or more, 9 or more, 10 or more, etc. protective base modifications (including where the protective base modifications are the same or different) may be incorporated into a dsDNA during a ligation reaction. In other instances, two or more different modifications, e.g., a permissive end-modification (e.g., a 5'-phosphate modification) and one or more protective base modifications may be present on a dsDNA segment that is incorporated into a dsDNA during a ligation reaction to generate a dsDNA containing two or more different modifications.

In some instances, dsDNA segments useful in a ligation reaction may be used in pairs, or higher order groupings, to incorporate two or more modifications into a dsDNA of the instant disclosure where each dsDNA segment of the pair contains at least one modification. Accordingly, a dsDNA segment may collectively contain two or more, e.g., 3 or more, 4 or more, 4 or more, 6 or more, 7 or more, 8 or more, 9 or more, 10 or more, etc. modifications (including where the modifications are the same or different). In some instances, one dsDNA segment of the pair may contain a permissive moiety and the other dsDNA segment may contain a protective moiety such that upon incorporation of the dsDNA segments into the dsDNA following a ligation reaction the produced dsDNA will contain a permissive moiety and a protective moiety, including e.g., where the produced dsDNA contains a first strand having the permissive moiety and a second strand having the protective moiety. In some instances, a single dsDNA segment may contain both a permissive moiety and a protective moiety, including where the permissive moiety and the protective moiety are on the same or different strands. The use of dsDNA segments is not limited to the introduction of protective and permissive moieties into separate strands as described but also includes e.g., where a dsDNA segment introduces permissive moieties into both strands, including e.g., where the dsDNA segment introduces permissive moieties into both strands but one or more protective moieties into only one strand.

dsDNA segments useful in the methods of the instant disclosure will vary in length depending on various factors including e.g., the particular technique used to generate the dsDNA segment, the desired end-use of the produced ssDNA (e.g., whether the dsDNA segments are configured to contain homology arms), etc. The length of a dsDNA segment of the instant disclosure may range from 15 bp or less to 4 kb or more up to 10 kb, including but not limited to e.g., 15 bp to 4 kb, 15 bp to 3.5 kb, 15 bp to 3 kb, 15 bp to 2.5 kb, 15 bp to 2 kb, 15 bp to 1.5 kb, 15 bp to 1 kb, 15 bp to 900 bp, 15 bp to 800 bp, 15 bp to 700 bp, 15 bp to 600 bp, 15 bp to 500 bp, 15 bp to 400 bp, 15 bp to 300 bp, 15 bp to 200 bp, 15 bp to 100 bp, 20 bp to 4 kb, 25 bp to 4 kb, 30 bp to 4 kb, 35 bp to 4 kb, 40 bp to 4 kb, 45 bp to 4 kb, 50 bp to 4 kb, 60 bp to 4 kb, 70 bp to 4 kb, 80 bp to 4 kb, 90 bp to 4 kb, 100 bp to 4 kb, 200 bp to 4 kb, 300 bp to 4 kb, 400 bp to 4 kb, 500 bp to 4 kb, 600 bp to 4 kb, 700 bp to 4 kb, 800 bp to 4 kb, 900 bp to 4 kb, 1 kb to 4 kb, 1.5 kb to 4 kb, 2 kb to 4 kb, 2.5 kb to 4 kb, 3 kb to 4 kb, 3.5 kb to 4 kb, 100 bp to 3 kb, 500 bp to 2.5 kb, 1 kb to 2 kb, etc.

The ligation of dsDNA segments of the instant disclosure may be blocked by a variety of methods, including but not limited to e.g., "sticky-end" ligation, "blunt-end" ligation, "T/A" containing substrate ligation, "splint" mediated ligation, and the like, the selection of which may depend on a number of factors including but not limited to e.g., the size of the fragments to be ligated, the sequence of the fragments to be ligated, the available ends of the fragments to be ligated, desired downstream processes, etc. By "sticky-end" ligation is meant an enzymatically mediated ligation reaction where the ligated ends of the dsDNA segments contain complementary 3' or 5' extensions (i.e., overlaps) prior to being ligated. By "blunt-end" ligation is meant an enzymatically mediated ligation reaction where the ligated ends of the dsDNA segments each contain a blunt end (i.e., a 3' or 5' end that does not contain an extension or terminally protruding nucleotide) prior to being ligated. By "T/A" containing substrate ligation is meant an enzymatically mediated ligation reaction where the ligated ends of the dsDNA segments contain complementary protruding terminal thymidine and adenine nucleotides. By "splint" mediated ligation is meant an enzymatically mediated ligation reaction where one dsDNA segment contains a 3' extension and the other dsDNA segment contains a 5' extension and the extensions are both homologous to a splint polynucleotide which, by hybridization mediates ligation of the extensions. Other strategies for dsDNA segment ligation may find use in the instant methods.

Enzymatically mediated ligation reactions will generally be performed with the use of one or more ligases, the selection of which will vary and may depend on e.g., the type of nucleic acid segments to be ligated, the ends of the nucleic acid segments to be ligated, the desired efficiency of the ligation reaction, the number and types of ends to be ligated, etc. The term "ligase" as used herein collectively refers to enzymes that catalyze the covalent joining of two adjacent ends of a nucleic acid molecule or molecules. For example, a nucleic acid ligase may catalyze the formation of a phosphodiester bond between juxtaposed 5' phosphate and 3' hydroxyl termini in single-stranded or double-stranded nucleic acid, including, .e.g., single-stranded DNA (ssDNA), double-stranded DNA (dsDNA), single-stranded RNA (ssRNA), and double-stranded RNA (dsRNA). Ligases may ligate nucleic acid hybridized to a complementary nucleic acid or may ligate in the absence of a complementary nucleic acid. Any convenient ligase may find use in the methods described herein including but not limited to, e.g., naturally occurring ligases, synthetic or recombinant ligases, mutant ligases, DNA ligases, RNA ligases, sticky-end ligases, blunt end ligases, nick-repair ligases, thermostable ligases, thermolabile ligases, T4 DNA ligase, T3 DNA ligase, T7 DNA ligase, *E. coli* DNA ligase, Taq DNA ligase, *Thermococcus* DNA ligase, Chlorella virus DNA Ligase, T4 RNA ligase 1, T4 RNA ligase 2, *Methanobacterium thermoautotrophicum* DNA/RNA ligase, and the like.

Following the production of a dsDNA by various methods, including e.g., PCR-based methods, ligation-based methods, etc., the produced dsDNA may or may not be modified to be compatible with a particular strand-selective degradation strategy as described herein. For example, in instances where one or more permissive motifs, one or more protective motifs or a combination of one or more permissive motifs and one or more protective motifs are incorporated into the dsDNA during the production method, e.g., during the PCR-based production method, during the ligation-based production method, etc., additional modification of the produced dsDNA may be unnecessary to make the produced dsDNA compatible with a desired strand-selective degradation strategy. In other instances, e.g., where one or more permissive motifs, one or more protective motifs or a combination of one or more permissive motifs and one or more protective motifs are not incorporated into the dsDNA during the production method, additional modification of the produced dsDNA may be necessary to make the produced dsDNA compatible with a desired strand-selective degradation strategy.

Various post-production (i.e., post-dsDNA production) modification methods may find use in the methods as described herein including but not limited to e.g., modifications to add one or more end-modifications (e.g., 5' phosphorylation to add a permissive 5' phosphate, 3' phosphorylation to add a protective 3' phosphate, attachment of one or more protective modified bases or spacers to a 3' end or 5' end or both 3' and 5' end of a strand of the dsDNA, etc.), modifications to remove one or more end-modifications (e.g., 5' dephosphorylation to remove a 5' phosphate, 3' dephosphorylation to remove a 3' phosphate, etc.), modifications to add a permissive or protective moiety to an internal base (i.e., a base not at a 3' or 5' terminal end) of the dsDNA, and the like. Phosphorylation and dephosphorylation may be achieved through the use of various kinases and phosphatases, respectively, including but not limited to e.g., T4 polynucleotide kinase, Shrimp Alkaline Phosphatase (SAP), Calf Intestinal Alkaline Phosphatase (CTAP), Bacterial Alkaline Phosphatase (*E. coli*), Antarctic Phosphatase, and the like.

In some instances, regardless of the method used to produce the dsDNA (e.g., PCR, ligation, etc.) and whether or not the produced dsDNA has been subsequently modified, the produced dsDNA may be modified to generate one or more particular dsDNA ends, including e.g., a blunt end, a 3' overhang or a 5' overhang, where such particular ends may serve as a permissive or protective moiety depending on the ability or inability of one or more downstream exonucleases to degrade the particular end(s). For example, in some instances, a blunt end may be introduced (e.g., by digesting the dsDNA with a restriction endonuclease that produces a blunt-end, fill-in of an overhang e.g., using T4 DNA polymerase, Klenow, etc.) and the blunt end may serve as a permissive or protective moiety depending on the ability or inability of one or more exonucleases utilized in the selective-strand digestion to degrade a blunt end. In some instances, a 5' overhang may be introduced (e.g., by digesting the dsDNA with a restriction endonuclease that produces a 5' overhang and the 5' overhang may serve as a permissive or protective moiety depending on the ability or inability of one or more exonucleases utilized in the selective-strand digestion to degrade a 5' overhang. In some instances, a 3' overhang may be introduced (e.g., by digesting the dsDNA with a restriction endonuclease that produces a 3' overhang and the 3' overhang may serve as a permissive or protective moiety depending on the ability or inability of one or more exonucleases utilized in the selective-strand digestion to degrade a 3' overhang.

Given the sequence specificity of restriction enzymes and the variety of cleavage patterns produced by the many available enzymes, specific nucleic acid sequences containing restriction enzyme recognition sites may be designed into the produced dsDNA in order to facilitate the generation of any desired end (e.g., blunt, 5' overhang or 3' overhang) in the resulting dsDNA molecule. As such the length of the overhanging strand in a 5' or 3' overhang may vary and may range from 1 nucleotide to 50 nucleotides or more including but not limited to e.g., 1 to 50 nucleotides, 1 to 40 nucleotides, 1 to 30 nucleotides, 1 to 25 nucleotides, 1 to 20 nucleotides, 1 to 19 nucleotides, 1 to 18 nucleotides, 1 to 17 nucleotides, 1 to 16 nucleotides, 1 to 15 nucleotides, 1 to 14 nucleotides, 1 to 13 nucleotides, 1 to 12 nucleotides, 1 to 11 nucleotides, 1 to 10 nucleotides, 1 to 9 nucleotides, 1 to 8 nucleotides, 1 to 7 nucleotides, 1 to 6 nucleotides, 1 to 5 nucleotides, 1 to 4 nucleotides, 1 to 3 nucleotides, 5 to 50 nucleotides, 5 to 40 nucleotides, 5 to 30 nucleotides, 5 to 25 nucleotides, 5 to 20 nucleotides, 5 to 19 nucleotides, 5 to 18 nucleotides, 5 to 17 nucleotides, 5 to 16 nucleotides, 5 to 15 nucleotides, 5 to 14 nucleotides, 5 to 13 nucleotides, 5 to 12 nucleotides, 5 to 11 nucleotides, 5 to 10 nucleotides, 5 to 9 nucleotides, 5 to 8 nucleotides, 5 to 7 nucleotides, 10 to 50 nucleotides, 10 to 40 nucleotides, 10 to 30 nucleotides, 10 to 25 nucleotides, 10 to 20 nucleotides, 10 to 19 nucleotides, 10 to 18 nucleotides, 10 to 17 nucleotides, 10 to 16 nucleotides, 10 to 15 nucleotides, 10 to 14 nucleotides, 10 to 13 nucleotides, 20 to 50 nucleotides, 30 to 50 nucleotides, 40 to 50 nucleotides, etc.

As will be readily understood, the described methods of producing dsDNA to be used in a strand-selective degradation method may be used independently of one another, meaning e.g., that a PCR-based method may not include a ligation step and a ligation-based method may not include a PCR step; however such methods are not necessarily mutually exclusive and may, in certain instances be combined. For example, in some instances, one dsDNA fragment generated by a PCR-based method may be attached to or incorporated into a second dsDNA fragment by a ligation reaction. In other instances, two dsDNA fragments joined by ligation may be amplified and/or extended through the use of a PCR.

Aspects of the instant disclosure include generating a single-stranded nucleic acid by selectively degrading one strand of a double-stranded nucleic acid having two strands that are sufficiently structurally different to allow degradation of one strand and not the other. Selective degradation of a single strand of a double-stranded nucleic acid may be blocked by a variety of methods, either singly or in combination, and will generally include selective enzymatic degradation of one strand of the nucleic acid based on one of more structural differences between the two strands of a double-stranded nucleic acid. As described above, such differences may be protective, meaning the difference protects one strand from degradation, or permissive, meaning that the difference allows a particular strand to be degraded.

Differences between the two nucleic acid strands may include a particular moiety present on one strand that is absent in the other strand where such a moiety may be a protective moiety or a permissive moiety. Such protective and permissive moieties may be incorporated into a double-stranded nucleic acid by a variety of methods including but not limited to e.g., those described above. The presence of a permissive moiety on a first strand and the absence of the permissive moiety on the second strand may cause a degradation enzyme to selectively degrade the first strand, leaving the second strand intact or essentially non-degraded. The presence of a protective moiety on a first strand and the absence of the protective moiety on the second strand may cause a degradation enzyme to selectively degrade the second strand, leaving the first strand intact or essentially non-degraded.

A double-stranded nucleic acid of the subject disclosure may include one or more protective moieties, one or more permissive moieties or a combination thereof. For example, in some instances, a double-stranded nucleic acid may include a single permissive moiety, i.e., where the single permissive moiety is present only on one strand. In some instances, a double-stranded nucleic acid may include a single protective moiety, i.e., where the single protective moiety is present only on one strand.

In some instances, the double-stranded nucleic acid may include a plurality of moieties, including a plurality of permissive moieties, a plurality of protective moieties or both permissive moieties and protective moieties. In such instances, permissive moieties will generally, but not exclusively, be present on one strand and protective moieties will be present on the other. In some cases, a permissive moiety and a protective moiety may both be present on the same strand, including e.g., where a strand contains a permissive moiety and a protective moiety, such that the effect of one moiety "overrides" the other including e.g., where the protective moiety prevents degradation of the strand despite the presence of a permissive moiety on the same strand. Accordingly, various combinations of permissive moieties and protective moieties within a single double-stranded nucleic acid and/or within a single strand of a double-stranded nucleic acid may find use in various cases. As referred to herein, the individual strands of a dsDNA may be referred to with reference to the herein disclosed method based on whether the particular strand is to be maintained to produce a single-stranded DNA (ssDNA) product. For example, references to a "product strand" will generally refer to the strand of a dsDNA that is maintained through the degradation process to produce a product ssDNA. Correspondingly, references to a "complementary strand" will generally refer to the strand of the dsDNA that is complementary to the product strand and thus the complementary strand will generally refer to the strand that is selectively degraded through the herein described method. In instances where the dsDNA contains at least some sequence encoding for a peptide or polynucleotide, the product strand may be the "sense strand" or "coding strand" (i.e., the strand that, from 5' to 3', contains the same sequence as the mRNA that is translated into the peptide or polynucleotide) and thus the complementary strand may be the "antisense strand" or "non-coding strand" (i.e., the strand that, from 5' to 3', serves as the template from which the mRNA is produced during transcription). In other instances, the product strand may be the antisense strand and the complementary strand may be the sense strand depending on the particular end purpose for the produced ssDNA.

A dsDNA of the instant disclosure need not necessarily include a sense strand and an antisense strand. For example, in some instances a dsDNA of the instant disclosure may not include a coding sequence and may only include non-coding sequence and thus may not include a sense strand or an antisense strand. In certain other instances where the dsDNA does not include coding sequence, the dsDNA may still be referred to as having a sense strand and an antisense strand, which designations may depend e.g., on coding sequence that neighbors the non-coding and thus has a sense and a non-sense strand. For example, a strand of a non-coding dsDNA that contains a promoter sequence or an intronic sequence may be referred to as a sense or antisense strand based on the sense/antisense strand designation applied to the coding sequence with which the promoter or intron is most closely associated. In other instances, a non-coding dsDNA, e.g., when not associated with a neighboring coding sequence, may not be referred to as having a sense or antisense strand.

Selective degradation of a strand of the dsDNA may be carried out with the use of one or more degradation enzymes where the particular enzyme(s) used will depend on the particular method employed. In some cases, degradation enzymes will be nucleases. Nucleases of the instant disclosure may be 5' exonucleases, 3' exonucleases or both 5' and 3' exonucleases. Nucleases of the instant disclosure may, in some instances, have endonuclease activity, either exclusively or in addition to exonuclease activity. In certain instances, nucleases of the instant disclosure do not have endonuclease activity.

Nucleases that may be employed in the methods of the instant disclosure include those exonucleases capable of digesting one or more strands of dsDNA having a blunt end, one or more dsDNA strands having a 5' extension, or one or more dsDNA strands having a 3' extension. In some instances, the exonuclease may be active upon dsDNAs having a blunt end and dsDNAs having a 5' extension. In certain instances, the exonuclease may be active upon dsDNAs having a blunt end and dsDNAs having a 3' extension. In certain instances, the exonuclease may be active upon dsDNAs having a 5' extension and dsDNAs having a 3' extension. In some instances, the exonuclease may be active upon dsDNAs having a blunt end, dsDNAs having 5' extension and dsDNAs having 3' extension.

Nucleases that may be employed in the methods of the instant disclosure may be strand-number dependent where strand-number dependent nucleases preferentially or exclusively degrade DNA that is either single-stranded or double-stranded. In some instances, a nuclease may be a single-strand dependent nuclease, e.g., a single-strand dependent exonuclease, that is only active upon or preferentially active upon double-stranded nucleic acids. Such single-strand dependent nucleases may find use in a variety of different applications, including but not limited to e.g., the removal of a 3' or 5' overhang on a dsDNA molecule (sometimes termed "DNA blunting"), removal of contaminating or excess single-stranded nucleic acids (e.g., RNA, oligonucleotides, etc.). Non-limiting examples of single-strand dependent nucleases include e.g., Exonuclease I, RecJ exonuclease and derivatives thereof, Exonuclease T, Exonuclease VII, Nuclease S1, Mung Bean Nuclease, etc. Single-strand dependent nucleases may also be directional having 5' to 3' nuclease activity or 3' to 5' nuclease activity.

Nucleases that may be employed in the methods of the instant disclosure may be a double-strand dependent nuclease, e.g., a double-strand dependent exonuclease, that is only active upon or preferentially active upon double-stranded nucleic acids. Such double-strand dependent nucleases may find use in a variety of different applications, including but not limited to e.g., degrading all or a portion of a double-stranded nucleic acid. Non-limiting examples of double-strand dependent nucleases include e.g., Lambda exonuclease, Exonuclease III, and the like. Double-strand dependent nucleases may also be directional having 5' to 3' nuclease activity or 3' to 5' nuclease activity. In some instances, a double-strand dependent nuclease may have partial activity on single-stranded substrates but, e.g., in the case of Lambda exonuclease, the activity may be at a greatly reduced rate as compared to the enzyme's activity on double-stranded substrate. Certain double-strand dependent nucleases, e.g., in the case of Exonuclease III, may have minor activity on double-stranded substrates of a particular direction, e.g., 3' extensions or 5' extensions, and/or the minor activity may be limited to single-stranded substrates below a particular length, e.g., less than 4 bases in length. Where active on DNA, a double-strand dependent exonuclease may be described as a dsDNA-dependent exonuclease, including 3' to 5' dsDNA dependent exonucleases and 5' to 3' dsDNA dependent exonucleases.

Nucleases active on both single- and double-stranded nucleic acids (i.e., strand-number independent nucleases), including e.g., strand-number independent exonucleases and strand-number independent endonucleases, may also find use in particular embodiments of the instant disclosure including but not limited to, e.g., where general digestion of nucleic acid or progressive shortening of a nucleic acid may be desired. Non-limiting examples of strand-number independent nucleases include e.g., Exonuclease V, Exonuclease VII (i.e., truncated Exonuclease VII), Nuclease BAL-31, DNase I, Micrococcal Nuclease, T5 Exonuclease, T7 Exonuclease, and the like.

In some instances, an exonuclease that may be employed in the methods of the instant disclosure may be end-dependent wherein the term "end-dependent" refers to those exonucleases that have exonuclease activity on one or more specific nucleic acid ends, depending e.g., on the chemistry of the end. Such end-dependent exonucleases find use, e.g., in selectively degrading one strand of a dsDNA where the strand to be degraded contains the specific nucleic acid end required for or preferred by the end-dependent exonuclease. End-dependent exonucleases include those that require a 5' phosphate for activity (i.e., 5' phosphate dependent exonucleases), including but not limited to e.g., lambda exonuclease, Terminator 5'-Phosphate-Dependent Exonuclease (Epicentre, Madison, Wis.), hSNM1 exonuclease, etc.

For example, referring briefly to the embodiment presented in FIG. 1, a linear dsDNA may be constructed by a PCR based method (e.g., using overlapping-PCR using three fragments as depicted). In the depicted overlap PCR, a left fragment (100), middle fragment (101), and right fragment (102) are amplified using an antisense primer containing a permissive modification (e.g., a 5' phosphate, depicted as (P)) that hybridizes to the right fragment (102). Thus, following PCR amplification, fragments 100, 101 and 102 are concatenated and possess a permissive modification on the antisense strand. Optionally, the produced PCR product can be purified prior to strand-selective degradation (e.g., using a DNA purification column as depicted (103)). Strand selective degradation may then be performed (104) using an end-dependent exonucleases (e.g., 5' phosphate-dependent exonuclease such as lambda exonuclease (LE) as depicted). Following strand-selective degradation, the generated ssDNA may, optionally be purified (e.g., using a DNA purification column as depicted (105)).

Neither the product strand nor the complementary strand of a dsDNA need necessarily contain a specific nucleic acid end on which an end-dependent nuclease acts. For example, in some instances, selective degradation of a single strand is mediated by one or more protective base modifications (including but not limited to e.g., a phosphorothioate internucleotide linkage) allowing the use of an exonuclease that functions independently of the type of ends (e.g., blunt, 3' overhang or 5' overhang, or presence or absence of a 5' phosphate, etc.) present on the dsDNA.

Conversely, where an end-dependent exonuclease is employed, neither strand need necessarily lack the specific permissive nucleic acid end on which an end-dependent nuclease acts. For example, in some instances, selective degradation of a single strand of a dsDNA where both strands contain the specific permissive nucleic acid end on which an end-dependent nuclease acts is mediated by one or more protective base modifications (including but not limited to e.g., a phosphorothioate internucleotide linkage) present in the product strand that block the activity of the end-dependent nuclease. Protective base modifications may be present anywhere on or within a subject nucleic acid, including but not limited to at the 3' or 5' end of a nucleic acid, near the end of the nucleic acid (e.g., within 50 bp or less, including e.g., 40 bp or less, 30 bp or less, 25 bp or less, 20 bp or less, 15 bp or less, 10 bp or less, etc., from the 3' or 5' end of the nucleic acid) or within the nucleic acid but not near an end (e.g., more than 10 bp, including e.g., more than 15 bp, more than 20 bp, more than 25 bp, more than 30 bp, more than 40 bp, more than 50 bp, etc., from the 3' or 5' end of the nucleic acid) or any combination thereof.

Nucleases that may be employed in the methods of the subject disclosure may include those that have activity that is blocked by one or more protective base modifications present on or in and/or introduced into a nucleic acid, including a dsDNA, including e.g., exonucleases having exonuclease activity that is blocked by one or more protective base modifications. Such nucleases find use in selectively protecting one strand of a dsDNA thus allowing the selective degradation of the other strand. Nucleases that may be blocked by one or more protective base modification include but are not limited to exonucleases blocked by one or more reverse nucleotide linkages (e.g., a 3'-3' linkage or a 5'-5' linkage), exonucleases blocked by one or more phosphorothioate linkages, exonucleases blocked by one or more 2'-O-Methyl base modifications (e.g., 2'-O Methyl Adenosine, 2'-O Methyl Cytosine, 2'-O Methyl Guanosine, 2'-O Methyl Uridine, etc.), exonucleases blocked by one or more 2' Fluoro base modifications (e.g., 2'-Fluoro deoxyadenosine, 2'-Fluoro deoxycytosine, 2'-Fluoro deoxyguanosine, 2'-Fluoro deoxyuridine, etc.), exonucleases blocked by one or more propyne modified nucleotides (e.g., propyne dC deoxycytosine, propyne dU deoxyuridine, etc.), exonucleases blocked by one or more phosphorylation modifications, exonucleases blocked by one or more methylphosphonate modifications, exonucleases blocked by one or more multi-carbon spacer modifications (e.g., C3 spacer modifications), etc.

Exonucleases blocked by one or more phosphorothioate linkages include but are not limited to e.g., lambda exonuclease, RecJ exonucleases, Exonuclease III, Exonuclease I, Exonuclease T, T7 exonuclease, those described in Spitzer & Eckstein (1988) Nucleic Acids Res. 16(24): 11691-11704, incorporated herein by reference in its entirety, and the like.

Useful protective base modifications include but are not limited to e.g., inverted bases used to produce base-linkage inversion, i.e., where the 3'-5' linkage of a base is inverted such that upon incorporation into a polynucleotide a 3'-3' or 5'-5' linkage is generated. Useful inverted bases include but are not limited to e.g., inverted adenine (idA) (e.g., 5'-inverted adenine (idA-5') or 3'-inverted adenine (idA-5')), inverted cytosine (idC) (e.g., 5'-inverted cytosine (idC-5') or 3'-inverted cytosine (idC-3')), inverted thymidine (idT) (e.g., 5'-inverted thymidine (idT-5') or 3'-inverted thymidine (idT-3')) and inverted guanine (idG) (e.g., 5'-inverted guanine (idG-5') or 3'-inverted guanine (idG-3')), inverted dideoxy nucleotides (e.g., inverted dideoxy adenine, inverted dideoxy cytosine, inverted dideoxy guanine and inverted dideoxy thymidine), mirror-image L-nucleotides (e.g., L-DNA, L-RNA), and derivatives and analogs thereof and the like.

Other useful protective base modifications include but are not limited to e.g., backbone modifications (e.g., phosphorothioate modifications), 2'-O-Methyl base modifications, 2' Fluoro base modifications, phosphorylation modifications (e.g., 3' phosphorylation), multi-carbon spacer modifications (e.g., C3 Spacer modifications (e.g., C3 Spacer Amidite (DMT-1,3-Propanediol), 1-(4,4'-Dimethoxytrityloxy)-propanediol-3-succinoyl-lcaa-CPG, 3-(4,4'-Dimethoxytrityloxy)propyl-1-[(2-cyanoethyl)-(N,N-diisopropyl)]-phosphoramidite, etc.), C9 Spacer modifications (e.g., 8-O-(4,4'-Dimethoxytrityl)-triethyleneglycol, 1-[(2-cyanoethyl)-(N,N-diisopropyl)]-phosphoramidite, etc.) C12 Spacer modifications (e.g., 12-(4,4'-Dimethoxytrityloxy)dodecyl-1-[(2-cyanoethyl)-(N,N-diisopropyl)]- phosphoramidite, etc.), and the like).

Useful protective base modifications may also include labels attached to the subject DNA strand that prevent degradation by one or more nucleases. Any useful nucleic acid label that prevents nuclease degradation may find use as a protective moiety as described herein, including but not limited to e.g., a biotin label. Labels may be incorporated into a subject DNA strand in a variety of ways including but not limited to e.g., by incorporating a labeled nucleotide (e.g., a biotin-labeled nucleotide) into a DNA strand, by ligating a biotin-labeled DNA fragment, by labeling a DNA strand by chemical attachment of the label to the strand, etc.

Methods of degrading a strand of a dsDNA, as described herein, used to produce a ssDNA of the instant disclosure may be used independently of one another; however such methods are not necessarily mutually exclusive and may, in certain instances be combined.

For example, in some instances, two or more different nucleases, e.g., two or more different exonucleases may be combined in a strand-selective degradation method. Reasons for including two or more nucleases in a strand-selective degradation method will vary and may in some instances include to increase the rate at which ssDNA is produced, overcome a limitation of a particular nuclease, etc.

In some instances, two different exonucleases may be used to prevent incomplete formation of a ssDNA due to specific sequences within the dsDNA that prevent procession of one or more of the exonucleases. Such combined use of two or more different exonucleases may be performed whether or not the sequence is known to contain a specific sequence that prevents the procession of one or more of the exonucleases. In some instances, the length of the dsDNA increases the probability that a specific sequence that prevents the procession of one or more of the exonucleases is present where longer dsDNAs will be more likely to contain such specific sequences. The length of dsDNAs that significantly increases the chances of the presence of a specific sequence that prevents the procession of one or more of the exonucleases will vary and may range from 200 by or more including but not limited e.g., 300 bp or more, 400 bp or more, 500 bp or more, 600 bp or more, 700 bp or more, 800 bp or more, 900 bp or more, 1 kb or more, etc. In other instances, the source of the dsDNA may make the dsDNA more or less likely to contain a specific sequence that prevents the procession of one or more of the exonucleases.

In some instances, a dsDNA may contain or is suspected to contain an exonuclease pause sequence, i.e., a sequence that slows and/or stops and/or disrupts the processivity of the exonuclease. Such exonuclease pause sequences may vary. In instances where a dsDNA contains or is suspected to contain an exonuclease pause sequence a second exonuclease may be used, including e.g., a second exonuclease that cleaves in the opposite direction (i.e., 3' to 5' or 5' to 3') as compared to the paused exonuclease.

In some instances, an exonuclease pause sequence may be a lambda pause sequence and e.g., where a dsDNA contains or is suspected to contain a lambda pause sequence, a second exonuclease may be used. The term "Lambda pause sequence" as used herein generally includes DNA sequences that, when present in a strand to be digested, negatively impact the processivity of lambda exonuclease of the subject strand. Examples of Lambda pause sequences include but are not necessarily limited to GGCG and GGCG containing sequences, GGCGA and GGCGA containing sequences, GGGCGGCGACCT and GGGCGGCGACCT containing sequences, e.g., as described in Perkins et al. (2003) Science. 301(5641): 1914-18, the disclosure of which is incorporated herein by reference in its entirety.

In some embodiments, a strand-specific digestion of a dsDNA may include the use of a lambda exonuclease and one or more 3' to 5' exonucleases, including but not limited to e.g., an end-dependent 3' to 5' exonuclease. In some instances, lambda exonuclease may be used in combination with Exonuclease III, where the two exonucleases may be added to a reaction at essentially the same time or at different times, including e.g., where lambda exonuclease is added to the reaction before the addition of exonuclease III. In some instances, the dsDNA may be incubated for some length of time with lambda exonuclease before the addition of exonuclease III, where the length of such an incubation will vary based on various factors and may range from 5 min. or less to an hour or more up to 2 hours, including but not limited to e.g., from 5 min. to 1 hour, from 10 min. to 1 hour, from 15 min. to 1 hour, from 20 min. to 1 hour, from 25 min. to 1 hour, from 30 min. to 1 hour, from 35 min. to 1 hour, from 40 min. to 1 hour, from 45 min. to 1 hour, from 5 min. to 55 min, from 5 min. to 50 min, from 5 min. to 45 min, from 5 min. to 40 min, from 5 min. to 35 min, from 5 min. to 30 min, from 5 min. to 25 min, from 5 min. to 20 min, from 5 min. to 15 min, from 10 min. to 50 min, from 15 min. to 45 min, from 20 min. to 40 min, from 25 min. to 35 min, etc. Such incubations may also be performed at a variety of temperatures including temperatures ranging from 20° C. to 65° C., including but not limited to e.g., from 20° C. to 65° C., from 20° C. to 60° C., from 20° C. to 55° C., from 20° C. to 50° C., from 20° C. to 45° C., from 20° C. to 42° C., from 20° C. to 40° C., from 20° C. to 37° C., from 25° C. to 65° C., from 25° C. to 60° C., from 25° C. to 55° C., from 25° C. to 50° C., from 25° C. to 45° C., 25° C. to 42° C., from 25° C. to 40° C., from 25° C. to 37° C., from 30° C. to 65° C., from 30° C. to 60° C., from 30° C. to 55° C., from 30° C. to 50° C., from 30° C. to 45° C., from 30° C. to 42° C., from 30° C. to 40° C., from 35° C. to 65° C., from 35° C. to 60° C., from 35° C. to 55° C., from 35° C. to 50° C., from 35° C. to 45° C., from 35° C. to 42° C., from 35° C. to 40° C., etc.

Figure 18:
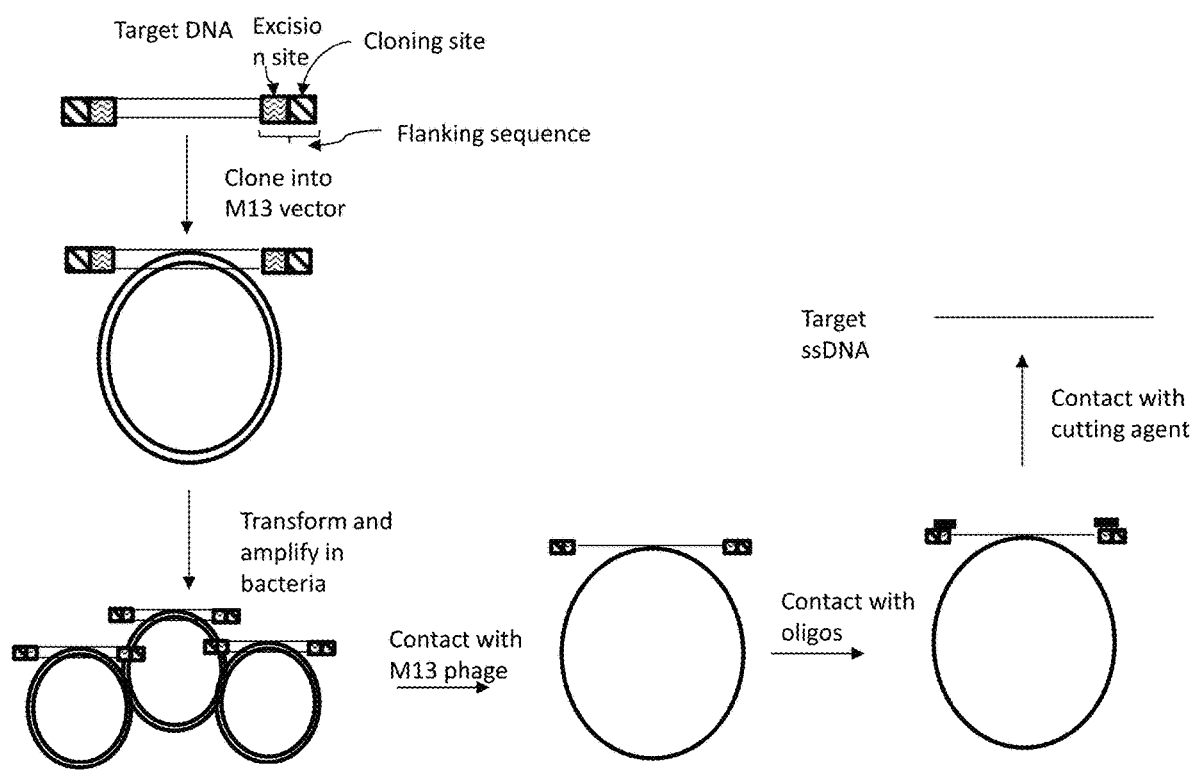
FIG. 18 depicts an embodiment of the methods of the disclosure for generating ssDNA using cloning and phage-based methods.

Production of Single-Stranded Nucleic Acids Using a Cloning and Phage-Based Method The disclosure provides for methods for generating a long ssDNA using a cloning and phage-based method (e.g., as described in FIG. 18). A target dsDNA of the disclosure may be generated (e.g., by any method of the disclosure, such as overlap PCR). The target dsDNA may include homology arms, as desired. In some instances, the target dsDNA may include flanking sequences (e.g., in addition to homology arms). The flanking sequences can be located at the ends of the target dsDNA. In some instances, the flanking sequences are 10, 20, 30, 40, 50 or more nucleotides in length. In some instances, the flanking sequences can be at most 10, 20, 30, 40, 50 in length. The flanking sequences can include any known sequence. The flanking sequence can be used for cloning and/or excision of the target dsDNA (or its corresponding ssDNA sequence). A flanking sequence can include one or more excision sites and one or more cloning sites, or any combination thereof. An excision site can include a restriction endonuclease cleavage site (e.g., BamH1, EcoR1). An excision site can include an arbitrary sequence that can be hybridized by a guide RNA, as described herein. The excision sites at each end of the target dsDNA can be the same. The excision sites at each end of the target dsDNA can be different from each other. The cloning sites at each end of the target dsDNA can be the same. The cloning sites at each end of the target dsDNA can be different from each other.

The target dsDNA may be cloned into a vector, such as into a plasmid or bacteriophage, for propagation. Cloning can be blocked by any method such as through TOPO Cloning, blunt end cloning, restriction enzyme digestion and ligation, and ligation-independent cloning (e.g., In-Fusion™ cloning system, Takara Bio USA, Mountain View, Calif.). Where a cloning method may use any extraneous (i.e., flanking) sequences to enable the cloning, those can be added to the cloning sites during generation of the target dsDNA, as desired.

In some instances, the target dsDNA is cloned into a vector for generating ssDNA, such as a phage vector, e.g., a bacteriophage vector, such as a vector derived from phage having a single stranded DNA genome, such as a vector derived from the filamentous phage vector, such as an M13 phage vector. The M13 phage is a filamentous bacteriophage that infects E. coli. The M13 genome encodes genes involved in phage DNA replication, phage capsid synthesis, and phage assembly. Replication of the phage genome results in phages harboring only one strand of the genome. The single-stranded nature of the M13 genome is well-suited for production of long ssDNAs. By using the M13 phage as a vector for cloning a target dsDNA, the target dsDNA can be produced in the single-strand form.

The employed vector, such as the M13 vector, can be engineered as desired. The employed vector, such as the M13 vector, can be engineered with a multiple cloning site, or any other feature suitable for use in the invention. The employed vector, such as the M13 vector, can be circular or linear.

The target dsDNA can be cloned into the vector at known cloning sites in the vector, for example, using the corresponding cloning sites in the target dsDNA. For example, the vector and the target dsDNA comprising cloning sites can both be contacted with one or more restriction endonucleases to generate complementary sticky ends, which may anneal and be ligated together. In another example, the M13 phage vector can be linear and comprise a cloning sequence at its 3' and 5' ends. A complementary cloning sequence can be added to the cloning sites of the target dsDNA. The target dsDNA can be contacted with the linearized M13 phage and inserted via transformation (e.g., In-Fusion™ cloning).

The vector comprising the target dsDNA may be transformed into a bacterial host cell (e.g., E. Coli, Top10, JM109, and competent cell suitable for M13 phage) for propagation. Bacterial transformation can be blocked by any suitable protocol, such as by natural competence for DNA uptake, chemical competence for DNA uptake, or by electroporation. Bacteria may be transformed by conjugation, in which genetic material is transferred horizontally between bacterial cells. Bacteria may be transformed by bacteriophage transduction, in which a bacteriophage transfers its genetic material into a host cell.

The bacteria transformed with the vector may amplify the vector. Amplified vector may be treated with M13 phage which can convert the double stranded vector to a single stranded vector and lyse the bacterial cells. Single stranded vector may be purified from the lysate using any method known in the art, for example, repeated centrifugation and treatment with Sodium Chloride and PEG-8000, miniprep kits, etc. The purified single stranded vector may be treated to excise the target ssDNA (i.e., originating from the target dsDNA). Various methods for excising the target ssDNA can be employed. Oligonucleotides can be hybridized to the excision site sequences in the target ssDNA, thereby forming double-stranded excision sites. These double-stranded excision sites can be contacted by a cleaving agent. The cleaving agent can be a restriction endonuclease or a CRISPR/Cas9 complex. The restriction endonuclease can cleave the double-stranded region, thereby excising the target ssDNA. In some instances, the double-stranded excision sites can be contacted by a CRISPR/Cas9 complex comprising a Cas9 protein and guide RNA complementary to the double-stranded excision site. The Cas9 protein can cut the double-stranded excision site, thereby liberating the target ssDNA molecule.

Produced Single-Stranded Nucleic acids and Methods of Use

Produced single stranded nucleic acids, such as ssDNA (e.g., produced by the methods of the disclosure, such as described above), may be of various lengths, as described above, and may be the same or essentially the same length as the dsDNA from which it was produced. In some instances, the produced ssDNA may be shorter than the dsDNA from which it is produced where, e.g., before or after strand selective degradation either the dsDNA or the produced ssDNA is cleaved and/or partially digested, e.g., through the use of one or more restriction enzymes or exonucleases. Produced ssDNA may be shortened for a variety reasons or as a result of modifying the produced ssDNA following strand selective degradation. For example, in some instances, a shortened ssDNA is produced as a result of removing one or more protective groups present on the end(s) of the ssDNA following strand selective degradation. Produced ssDNA may or may not have an attached permissive moiety. Accordingly, permissive moieties present in a dsDNA prior to selective strand degradation may or may not persist in the ssDNA following degradation. For example, in some instances, a permissive moiety may be present on the complementary strand that is degraded during selective strand degradation and thus will not be present on the non-degraded ssDNA product strand. In some instances, a permissive moiety may be present on the product strand but degradation of the product strand may be inhibited by some other means, e.g., the presence of one or more protective moieties on the product strand and, as such, the produced ssDNA product strand may contain a permissive moiety following degradation.

Produced ssDNA may or may not have an attached protective moiety. Accordingly, protective moieties present in a dsDNA prior to selective strand degradation may or may not be allowed to persist in the ssDNA following degradation. For example, in some instances, a protective moiety may be present on the product strand of the dsDNA such that following degradation the protective moiety persists on the produced ssDNA. In some instances, following degradation a protective moiety present at or near the end of the product strand may be removed e.g., through partial digestion or enzymatic cleavage of the product strand near the site of the protective moiety. For example, in some instances the produced ssDNA may be configured to contain one or more restriction endonuclease recognition sites for removal of one or more protective moieties positioned at or near the end(s) of the ssDNA such that, upon introduction of an appropriate sequence specific ssDNA restriction endonuclease, the one or more protective moieties are removed. Removal of protective moieties from produced ssDNA is not limited to site specific restriction enzyme digestion and various alternative techniques for removing protective moieties may be employed depending on the particular protective moiety used and/or the relative position of the moiety on the produced ssDNA. As such, produced ssDNAs, including those produced from dsDNAs containing protective moieties, may be generated that no longer contain protective moieties. It will be recognized, however, that for particular downstream applications protective moieties need not necessarily be removed.

Following the production of a dsDNA to be used in generating a ssDNA, as described herein, the produced dsDNA may be purified or washed prior to one or more subsequent steps. Useful methods of purifying and/or washing generated dsDNA molecules include but are not limited to e.g., column-based dsDNA purification (e.g., DNA purification columns), nucleic acid extraction methods (e.g., alcohol extraction), gel-based purification methods, and the like.

Following the production of a ssDNA, as described herein, the produced ssDNA product strand may be purified or washed, e.g., prior use in a homologous recombination reaction. Useful methods of purifying and/or washing generated ssDNA molecules include but are not limited to e.g., column-based dsDNA purification (e.g., DNA purification columns), nucleic acid extraction methods (e.g., alcohol extraction), gel-based purification methods, and the like.

Following the production of ssDNA, as described herein, the produced ssDNA product strand may be analyzed, e.g., to verify the identity of the ssDNA product, to verify the length of the ssDNA product, to verify the strandedness of the ssDNA product, to determine the purity of the ssDNA product, etc. Any convenient method for analyzing a produced ssDNA may find use in such methods including but not limited to e.g., gel electrophoresis (e.g., agarose gel electrophoresis), PCR-based analysis methods, hybridization-based analysis methods, nucleic acid sequencing based-analysis methods, chromatography-based methods (e.g., Ion Exchange HPLC, Reverse Phase HPLC, Ultra Performance (UPLC), etc.), mass spectrometry-based methods (MALDI-TOF, ESI-MS, etc.). Various methods of analyzing the produced ssDNA may be performed independently or may be used in combination.

Utility

The produced ssDNA molecules may find various uses in biochemical, molecular biological and genetic research endeavors, as well as, clinical endeavors, including e.g., clinical molecular genetics and gene therapy. Produced ssDNA molecules may also find use in biotechnological and industrial settings.

In some instances, the produced ssDNA may be of sufficient length to be employed as a single stranded DNA oligonucleotide in a PCR amplification reaction, e.g., as a single stranded DNA primer. Sufficient lengths of ssDNA produced for use as a DNA primer include but are not limited to those commonly employed primer lengths described above. Other uses for ssDNA produced according to the methods described herein include but are not limited to e.g., probes for in situ hybridization, probes for microarray analysis, template strands for sequencing-by-synthesis (e.g., pyrosequencing), and the like. When utilized as a probe, the produced ssDNA may be labeled either for direct or indirect detection where suitable labels include but are not limited to e.g., fluorescent labels (e.g., fluorescent small molecules (e.g., fluorescein, DAPI, Texas Red, etc.), fluorescent proteins (e.g., GFP, DsRed, etc.), quantum dots, etc.), colorimetric or chromogenic labels, enzymatic substrate labels (e.g., substrates for alkaline phosphatase, substrates for horseradish peroxidase, substrates for tyramide amplification, etc.), affinity labels (e.g., biotin/streptavidin labels), micro-particle labels (e.g., gold particles, etc.), radioactive labels, and the like.

ssDNA molecules generated according to the methods as described herein may also be used in the assembly of larger DNA molecules. For example, in some instances, a ssDNA molecule may be configured to hybridize with one or more other completely or partially single stranded DNA molecules to facilitate the assembly of a larger dsDNA molecule. In some instances, following hybridization of a ssDNA with one or more complementary ssDNAs or partially single stranded DNAs the separate molecules may be joined covalently, e.g., through ligation and/or enzymatic polymerization. In some instances, long dsDNA molecules of desired sequence may be produced by generating a plurality of ssDNA molecules according to the methods described herein and assembling the plurality of ssDNA molecules into a long dsDNA based on sequence specific hybridization between the produced ssDNA molecules and subsequent ligation reactions. In some instances, two or more short ssDNA molecules may be assembled into a desired dsDNA. In some instances, two or more long ssDNA molecules, as described herein, may be assembled into a long dsDNA. Such processes find use in a variety of nucleic acid assembly applications including e.g., synthetic biology where long ssDNA molecules may be assembled to construct or reconstruct or recombine entire expression cassettes, entire genes, entire genetic loci, entire chromosomes, or entire genomes, etc.

The useful applications of ssDNA produced according to the methods described herein are not limited to macromolecule synthesis and detection assays but instead also include functional applications. Functional applications of ssDNA molecules may be performed in vitro or in vivo. In some instances, ssDNA molecules may be employed to block the function of a target gene, including e.g., where the ssDNA molecule is configured as an antisense DNA oligonucleotide. For example, antisense ssDNA oligonucleotides may be used to block the function of a RNA molecule expressed from a target gene or a non-coding RNA by hybridizing to the RNA and directing RNase H mediated-degradation of the RNA.

In some functional applications, the ssDNA may provide a coding or regulatory sequence to an organism or cell, including e.g., where the ssDNA contains a coding sequence that is heterologous to the organism or cell. Heterologous coding sequences may encode proteins or peptides that alter the normal functions of the organism or cell or encode protein labels for identifying or tracking and the organism or cell, or portions thereof. Regulatory sequences that may be provided on a produced ssDNA include but are not limited to e.g., promoters, enhancers, transcription factor binding sites, etc. In some instances, sufficiently long ssDNA molecules may provide both coding sequences and non-coding sequences that may or may not include regulatory sequences.

The produced ssDNA may include one or more single-stranded portions of a gene of interest (GOI), the GOI portion of the ssDNA may be full length or may be a portion of a GOI including e.g., one or more domains of a GOI. In some instances a GOI may be or may include a cDNA encoding a protein of interest. Given the versatility of the described method, any desired GOI or portion thereof may be included in a particular ssDNA. Non-limiting examples of GOIs that may be included, in whole or in part, in a ssDNA of the instant disclosure include but are not limited to e.g., genes encoding fluorescent proteins, genes encoding transcription factors, genes encoding structural proteins, genes encoding metabolic proteins, genes encoding signaling molecules, genes encoding therapeutic proteins, genes encoding drug-selection markers, and the like.

Methods are herein provided for producing a desired ssDNA and using the produced ssDNA to efficiently modify genomic DNA. Methods of modifying genomic DNA with a ssDNA of the instant disclosure will generally involve the use of homologous recombination (i.e., homology directed repair) to modify the genomic DNA. Genomic DNA to be modified by the subject method will vary and may include but is not limited to e.g., the genomic DNA of an animal model (e.g., used in a research setting), the genomic DNA of a plant (e.g., used in a research setting or an agricultural setting), the genomic DNA of a bacteria (e.g., used in a research setting, an agricultural setting, an industrial setting or a medical setting), the genomic DNA of an archaea (e.g., used in a research setting, an agricultural setting, an industrial setting or a medical setting),), the genomic DNA of a virus (e.g., used in a research setting, an agricultural setting, an industrial setting or a medical setting), the genomic DNA of livestock (e.g., used in a research setting, an agricultural setting, an industrial setting or a medical setting), the genomic DNA of a pet or companion animal (e.g., used in a veterinary setting), the genomic DNA of a human subject (e.g., used in a medical or clinical setting), and the like.

Animal DNA genomes that may be modified according to the methods as described herein include but are not limited to e.g., mammalian genomes including e.g., murines (rats, mice), non-human primates, humans, canines, felines, ungulates (e.g., equines, bovines, ovines, porcines, caprines), lagomorphs, etc. In some instances, a modified genome may be a plant genome, an invertebrate (e.g., a cnidarian, an echinoderm, a worm, a fly, etc.) genome, a non-mammalian vertebrate (e.g., a fish (e.g., zebrafish, puffer fish, gold fish, etc.)) genome, an amphibian (e.g., salamander, frog, etc.) genome, a reptile genome, a bird genome, a an ungulate (e.g., a goat, a pig, a sheep, a cow, etc.) genome, a rodent (e.g., a mouse, a rat, a hamster, a guinea pig) genome, etc.

Methods of homology directed repair of a DNA genome may be performed for various purposes including but not limited to e.g., the introduction of a heterologous gene or gene fragment into the genome of an organism, the correction of a deleterious mutation in the genome of an organism, the introduction of a mutation, and the like. Following the homologous recombination event the genome may be modified and thus referred to as a modified genome.

Homology directed repair of a subject DNA genome may be performed in vitro, ex vivo, in utero or in vivo.

Produced ssDNA utilized in modification of genomic DNA may include, and thus incorporate into the target genome, one or more coding sequences (including e.g., exon coding sequences, cDNA coding sequences, synthetic coding sequences, etc.), one or more non-coding sequences (including e.g., a promoter, an enhancer, an intron, etc.). In some instances, the ssDNA includes a coding sequence correcting one or more deleterious mutations present in the target genome. In some instances, the ssDNA includes a noncoding sequence correcting one or more deleterious mutations present in the target genome.

Methods of modifying genetic DNA by homology directed repair using a ssDNA of the instant disclosure will generally, but not necessarily, include the use of a nuclease for use in cleaving the target genome in order to facilitate or expedite the homology directed repair. In some embodiments, the target genomic DNA is contacted with a produced ssDNA, having homology arms that are homologous to targeted regions of the genomic DNA, and one or more genome-cleaving nucleases. Depending on the particular method employed, such contacting may be performed in vitro, ex vivo, in utero or in vivo.

Useful genome targeting nucleases will vary and the selection of which may depend on e.g., the genomic DNA to be modified (e.g., the source of the genomic DNA to be modified and, e.g., whether human genomic DNA or animal genomic DNA is to be modified), the type of genomic modification being performed, etc. Any convenient genome targeting nuclease may find use in the methods as described herein.

In some instances, an instant method of genomic DNA modification may include the use of a Cas9 nuclease, including natural and engineered Cas9 nucleases. Useful Cas9 nucleases include but are not limited to e.g., Streptococcus pyogenes Cas9 and variants thereof, *Staphylococcus aureus* Cas9 and variants thereof, *Actinomyces naeslundii* Cas9 and variants thereof, Cas9 nucleases also include those discussed in PCT Publications Nos. WO 2013/176772 and WO2015/103153 and those reviewed in e.g., Makarova et al. (2011) *Nature Reviews Microbiology* 9: 467-477, Makarova et al. (2011) Biology Direct 6:38, Haft et al. (2005) PLOS Computational Biology 1:e60 and Chylinski et al. (2013) RNA Biology 10: 726-737, the disclosures of which are incorporated herein by reference in their entirety. In some instances, a non-Cas9 CRISPR nuclease may be employed, including but not limited to e.g., Cpf1.

Cas9 nucleases are used in the CRISPR/Cas9 system of genomic DNA modification. In the CRISPR/Cas9 system a chimeric RNA containing the target sequence (i.e., the "guide RNA" or "small guide RNA (sgRNA)", which collectively contains a crRNA and a tracrRNA) guides the Cas9 nuclease to cleave the DNA at a specific target sequence defined by the sgRNA. The synthesis of only a 20 bp guide RNA is required to program the nuclease. The specificity, efficiency and versatility of targeting and replacement of homologous recombination is greatly improved through the combined use of various homology-directed repair strategies and CRISPR nucleases (see e.g., Gratz et al. (2014) Genetics. 196(4) 961-971; Chu et al. (2015) Nature. 33:543-548; Hisano et al. (2015) Scientific Reports 5: 8841; Farboud & Meyer (2015) Genetics, 199: 959-971; Merkert & Martin (2016) Stem Cell Research 16(2): 377-386; the disclosures of which are incorporated herein by reference in their entirety). The CRISPR system offers significant versatility in targeting of genomic modification in part because of the small size and high frequency of necessary sequence targeting elements with host genomes. CRISPR guided Cas9 nuclease requires the presence of a protospacer adjacent motif (PAM), the sequence of which depends on the bacteria species from which the Cas9 was derived (e.g. for *Streptococcus pyogenes* the PAM sequence is "NGG") but such sequences are common throughout various target genomes. The PAM sequence directly downstream of the target sequence is not part of the guide RNA but is obligatory for cutting the DNA strand. However, synthetic Cas9 nucleases have been generated with novel PAM recognition, further increasing the versatility of targeting.

CRISPR related components, including Cas9 nucleases and non-Cas9 nucleases, are readily available as encoding plasmids from various sources including but not limited to those available from Addgene (Cambridge, Mass.) which may be ordered online at www(dot)addgene(dot)org.

In methods of genome modification with a ssDNA as described herein CRISPR nucleases, including Cas9 nucleases and non-Cas9 nucleases, may be provided as a protein, including e.g., where such protein contains an attached transduction domain or is provided with one or more transduction reagents, or a combination thereof. In some instances, a CRISPR nuclease may be expressed from a plasmid or integrated into a host genome. Various methods of performing CRISPR/Cas9 mediated genome modification, including the conditions permissive for CRISPR/Cas9 mediated homology-directed repair in various settings, including in vivo and in vitro settings include but are not limited to e.g., those described in the references cited above.

Exogenous cellular materials can be introduced to cells using any convenient protocol. Materials which may be added to cells include nucleic acids and proteins. Transfection is the introduction of foreign DNA into cells by methods which are known in the art. These methods include, but are not limited to, natural competence for nucleic acid uptake in bacteria, transformation, transfection with transfection reagents, electroporation, or in gesicles or micelles. Nucleic acids may be introduced into cells in single- or double-stranded form such as ssDNA fragments, dsDNA fragments, or as a plasmid. Exogenous proteins can be added to cells in any way known in the art. Proteins may be introduced into cells in a complex with a nucleic acid, such as with ribonucleoproteins, and electroporated into cells. In some instances, a CRISPR/Cas9 ribonucleoprotein complex may be electroporated into cells with along with ssDNA or dsDNA.

Proteins may be introduced into cells via transduction domains known in the art. For example, a protein transduction domain may be a canonical protein transduction domain or a distributed protein transduction domain. By distributed it is meant that the amino acids of the protein transduction domain are distributed throughout the polypeptide, rather than sequestered as a discrete domain of consecutive amino acids within the polypeptide. As such protein transduction domain is made up of multiple non-sequential amino acid residues that, upon folding of the protein into a three-dimensional structure, make up a "basic-patch" on the surface of the protein that imparts protein transduction activity to the protein. In other words, the distributed protein transduction domain arises from the interaction of multiple non-sequential residues which, when the protein assumes a tertiary structure, are part of a basic patch. A "basic patch" is a surface region of a folded protein that comprises 3 or more, such as 5 or more, including 10 or more number basic amino acid residues, i.e., histidine (H), lysine (K) or arginine (R). The total number of basic residues in a given basic patch may vary, ranging in some instances from 2 to 50, such as 3 to 30 and including 5 to 20, e.g. 2 or more residues, 3 or more residues, 4 or more residues, 5 or more residues, in some instances 6 or more residues, 8 or more residues, or 10 or more residues, e.g. 20 residues or more.

In some instances, an instant method of genomic DNA modification may include the use of a zinc-finger nuclease (ZFN). ZFNs consist of the sequence-independent FokI nuclease domain fused to zinc finger proteins (ZFPs). ZFPs can be altered to change their sequence specificity. Cleavage of targeted DNA requires binding of two ZFNs (designated left and right) to adjacent half-sites on opposite strands with correct orientation and spacing, thus forming a FokI dimer. The requirement for dimerization increases ZFN specificity significantly. Three or four finger ZFPs target~9 or 12 bases per ZFN, or~18 or 24 bases for the ZFN pair. ZFN pairs have been used for gene targeting at specific genomic loci in insect, plant, animal and human cells. The specificity, efficiency and versatility of targeting and replacement of homologous recombination is greatly improved through the combined use of various homology-directed repair strategies and ZFNs (see e.g., Urnov et al. (2005) Nature. 435(7042): 646-5; Beumer et al (2006) Genetics. 172(4): 2391-2403; Meng et al (2008) Nat Biotechnol. 26(6): 695-701; Perez et al. (2008) Nat Biotechnol. 26(7): 808-816; Hockemeyer et al. (2009) Nat Biotechnol. 27(9): 851-7; the disclosures of which are incorporated herein by reference in their entirety).

In general, one ZFN site can be found every 125-500 bp of a random genomic sequence, depending on the assembly method. Methods for identifying appropriate ZFN targeting sites include computer-mediated methods e.g., as described in e.g., Cradick et al. (2011) BMC Bioinformatics. 12: 152, the disclosure of which is incorporated herein by reference in its entirety.

ZFN related components, including ZFN nucleases, are readily available as encoding plasmids from various sources including but not limited to those available from Addgene (Cambridge, Mass.) which may be ordered online at www(dot)addgene(dot)org.

In methods of genome modification with a ssDNA as described herein ZFN nucleases, may be provided as a protein, including e.g., where such protein contains an attached transduction domain or is provided with one or more transduction reagents, or a combination thereof. In some instances, a ZFN nuclease may be expressed from a plasmid or integrated into a host genome. Various methods of performing ZFN mediated genome modification, including the conditions permissive for ZFN mediated homology-directed repair in various settings, including in vivo and in vitro settings include but are not limited to e.g., those described in the references cited above.

In some instances, an instant method of genomic DNA modification may include the use of a transcription activator-like effector nuclease (TALEN). Similar in principle to the ZFN nucleases, TALENs utilize the sequence-independent FokI nuclease domain fused to Transcription activator-like effectors (TALEs) proteins that, unlike ZNF, individually recognize single nucleotides. TALEs generally contain a characteristic central domain of DNA-binding tandem repeats, a nuclear localization signal, and a C-terminal transcriptional activation domain. A typical repeat is 33-35 amino acids in length and contains two hypervariable amino acid residues at positions 12 and 13, known as the "repeat variable di-residue" (RVD). An RVD is able to recognize one specific DNA base pair and sequential repeats match consecutive DNA sequences. Target DNA specificity is based on the simple code of the RVDs, which thus enables prediction of target DNA sequences. Native TALEs or engineered/modified TALEs may be used in TALENs, depending on the desired targeting.

TALENs can be designed for almost any sequence stretch. Merely the presence of a thymine at each 5' end of the DNA recognition site is required. The specificity, efficiency and versatility of targeting and replacement of homologous recombination is greatly improved through the combined use of various homology-directed repair strategies and TAL-ENs (see e.g., Zu et al. (2013) Nature Methods. 10: 329-331; Cui et al. (2015) Scientific Reports 5: 10482; Liu et al. (2012) J. Genet. Genomics. 39: 209-215, Bedell et al. (2012) Nature. 491: 114-118, Wang et al. (2013) Nat. Biotechnol. 31: 530-532; Ding et al. (2013) Cell Stem Cell. 12: 238-251; Wefers et al. (2013) Proc. Natl. Acad. Sci. U. S. A., 110: 3782-3787; the disclosures of which are incorporated herein by reference in their entirety).

TALEN related components, including TALEN nucleases, are readily available as encoding plasmids from various sources including but not limited to those available from Addgene (Cambridge, Mass.) which may be ordered online at www(dot)addgene(dot)org.

In methods of genome modification with a ssDNA as described herein TALEN nucleases, may be provided as a protein, including e.g., where such protein contains an attached transduction domain or is provided with one or more transduction reagents, or a combination thereof. In some instances, a TALEN nuclease may be expressed from a plasmid or integrated into a host genome. Various methods of performing TALEN mediated genome modification, including the conditions permissive for TALEN mediated homology-directed repair in various settings, including in vivo and in vitro settings include but are not limited to e.g., those described in the references cited above.

In some instances, the specificity and/or efficiency of genome modification, e.g., as mediated by one or more CRISPR nucleases, ZFNs, TALENs, etc., may be improved through the use of a ssDNA with homology arms that are 100 bp or longer, including but not limited to e.g., 150 bp or longer, 200 bp or longer, 250 bp or longer, 300 bp or longer, 350 bp or longer, 400 bp or longer, 450 bp or longer, 500 bp or longer, 550 bp or longer, 600 bp or longer, 650 bp or longer, 700 bp or longer, 750 bp or longer, 800 bp or longer, etc. In some instances, the use of a ssDNA as described herein in a genome modification, e.g., as mediated by one or more CRISPR nucleases, ZFNs, TALENs, etc., may reduce or produce essentially no background, where the amount of background may be determined by introducing the ssDNA in the absence of the nuclease.

The specificity and/or efficiency of homology directed repair using a ssDNA, as described herein, in a genome modification, e.g., as mediated by one or more CRISPR nucleases, ZFNs, TALENs, etc., may be determined by an convenient means including but not limited to e.g., identifying a reporter gene (e.g., a fluorescent reporter) expressed from the ssDNA, e.g., through the use of microscopic of flow cytometric methods (e.g., FACS). In some instances, the successful integration of a ssDNA by genome modification may be determined by sequencing e.g., by sequencing the targeted insertion site of the genome or by qualitative or quantitative sequencing of a plurality of genomes upon which genome modification was performed.

Kits

Also provided are kits having one or more components and/or reagents and/or devices for practicing one or more of the above-described methods. The subject kits may vary greatly. Kits of interest include those having one or more reagents mentioned above, and associated devices, with respect to the methods of generating a ssDNA and/or using a ssDNA in an appropriate application, including e.g., modifying a DNA genome with a ssDNA.

Kits of the instant disclosure may include one or more nucleic acids containing a permissive or protective moiety, or a combination thereof, for generating a dsDNA containing the permissive or protective moiety, or a combination thereof. The subject kits may further include one or more nucleases, including but not limited to e.g., an exonuclease for selective-strand degradation, a genome-targeting nuclease, etc. In some instances, a subject kit will include one or more exonucleases for generating a ssDNA by selective-strand degradation and a genome targeting nuclease for homology directed repair-based integration of the ssDNA into the genome or correction of the genome using the ssDNA. Nucleases of the subject kits may be provided in protein form or may be expressible from a plasmid encoding the nuclease.

The subject kits may contain components and/or additional reagents configured for PCR-based generation of a dsDNA containing a permissive moiety, a protective moiety or a combination thereof. The subject kits may contain components and/or additional reagents configured for ligation-based generation of a dsDNA containing a permissive moiety, a protective moiety or a combination thereof. The subject kits may contain components and/or additional reagents configured for both PCR-base and ligation-based generation of a dsDNA containing a permissive moiety, a protective moiety or a combination thereof.

The subject kits may include components and/or additional reagents configured for cloning and phage-based methods of generating ssDNA of the disclosure, e.g., as described above. For example, the subject kit can include a circularized or linearized M13 vector. The M13 vector can include a multiple cloning site. The kit can omc;ide competent bacteria for propagation of the M13 vector. The kit can include DNA extraction reagents for recovering the generated ssDNA. The kit can include one or more restriction endonucleases, Cas9 proteins, and guide RNAs, or any combination thereof.

In addition to the above components, the subject kits may further include (in some embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another form of these instructions is a computer readable medium, e.g., diskette, compact disk (CD), portable flash drive, Hard Drive etc., on which the information has been recorded. Yet another form of these instructions that may be present is a website address which may be used via the internet to access the information at a removed site.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech.

Example 1

PCR-Based Production of Long ssDNA Donor

Linear double-stranded DNA donor was constructed by an overlapping-PCR (20-base pair (bp) each) of three fragments. For general reference, the instant example essentially employs an embodiment of the broad method as presented in the schematic of FIG. 1. A GAPDH left-arm fragment (222-bp (200-bp homology arm plus an additional 2 bp to adjust the reading frame for translation and 20-bp of overlap with the sequence encoding AcGFP1) (gBlocks, Integrated DNA Technologies (IDT), Coralville, Iowa)), a middle fragment encoding AcGFP1 (717-bp, generated by PCR), and a GAPDH right-arm fragment (220-bp (20-bp overlap with the sequence encoding AcGFP1 plus the 200-bp homology arm) (gBlocks, IDT) were amplified using overlap PCR employing a 5' phosphorylated antisense primer priming the GAPDH right-arm template. The AcGFP1 encoding sequence contained no 5' promoter sequence or start codon necessary for independent expression. The produced PCR product was purified using a DNA purification column.

Figure 2:
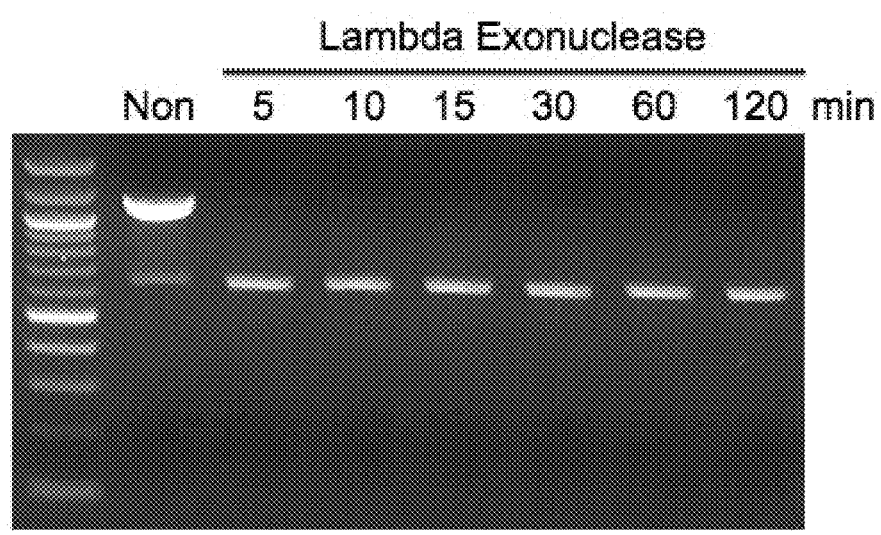
FIG. 2 depicts strand-selective lambda exonuclease digestion of a dsDNA according to certain embodiments as describe herein.

To selectively degrade the 5'-phosorylated antisense strand, the linear double-stranded product of the PCR was treated with Lambda exonuclease (LE) at 37° C. for various times. The resulting sense fragment was purified and analyzed by agarose-gel electrophoresis and confirmed to be single-stranded (FIG. 2).

Figure 3:
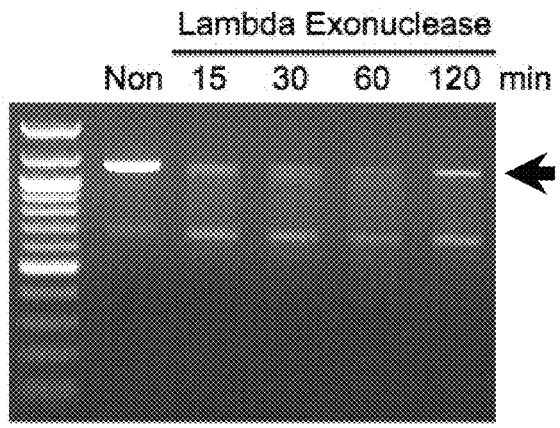
FIG. 3 depicts strand-selective lambda exonuclease digestion of a dsDNA containing a lambda exonuclease pause sequence according to certain embodiments as describe herein.
Figure 5:
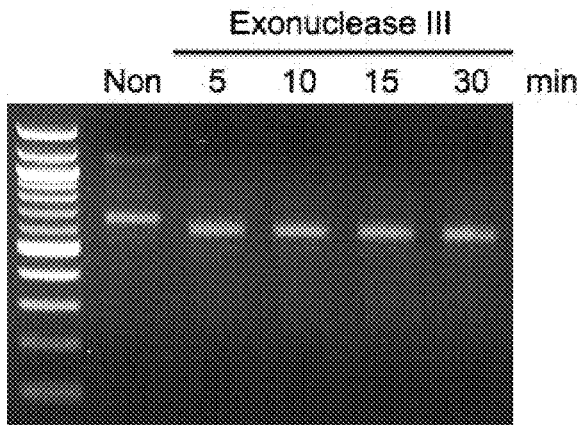
FIG. 5 depicts strand-selective Exonuclease III digestion of a dsDNA containing an exonuclease pause sequence according to certain embodiments as describe herein.
Figure 4:
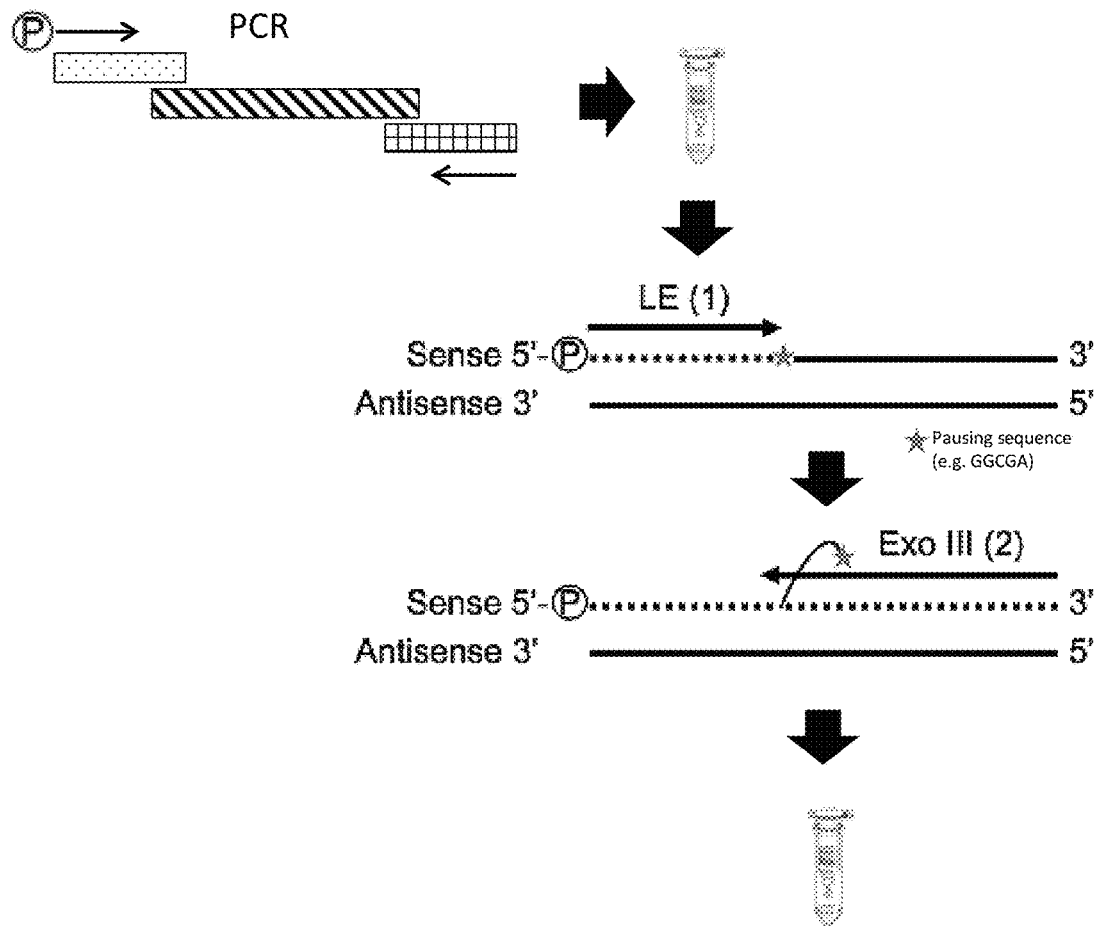
FIG. 4 depicts a schematic representation of a procedure for the generation of a dsDNA and subsequent strand-selective degradation using two exonucleases to produce a ssDNA according to certain embodiments as describe herein.

Production of the single-stranded antisense strand was performed in generally the same manner as described above, except a 5' phosphorylated sense primer priming the GAPDH left-arm template was used. Analysis by agarose-gel electrophoresis of the produced antisense ssDNA strand showed the presence of dsDNA even after 120 min. of Lambda exonuclease digestion (FIG. 3, arrow), indicating pausing of the lambda exonuclease. Analysis of the sequence of the sense strand revealed the presence of six Lambda exonuclease pausing sequences (GGCGA). Digestion of the sense-strand of dsDNA PCR product was performed again starting with Lambda exonuclease treatment at 37° C. for 30 min, at which point Exonuclease III and the corresponding Exonuclease III buffer were added to the digestion and the reaction mixture was incubated at 37° C. for various times up to 30 min (FIG. 4). The resulting fragment was analyzed by gel electrophoresis and found to contain only ssDNA product (FIG. 5).

Example 2

Modification of Genomic DNA

Figure 6:
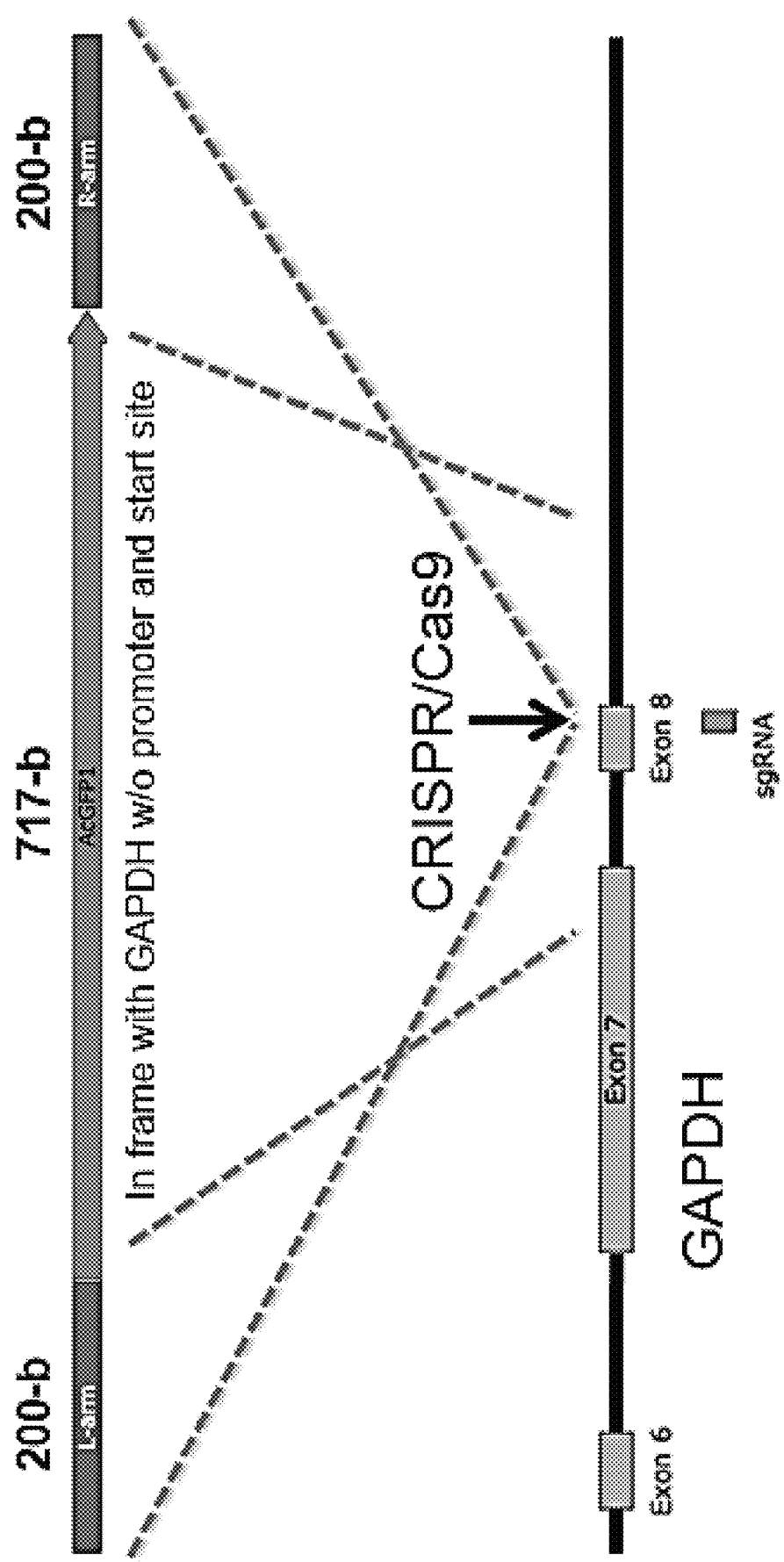
FIG. 6 depicts a schematic representation of a strategy for targeted integration of a construct into a target locus using the CRISPR/Cas9 system and a ssDNA of the instant disclosure.
Figure 7:
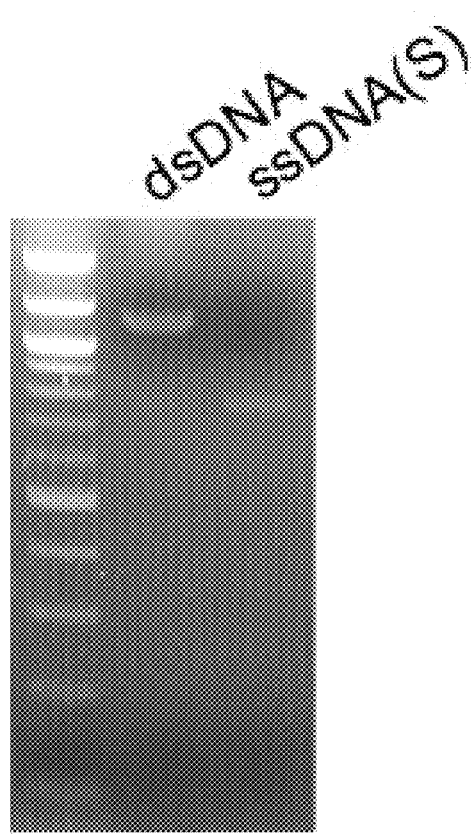
FIG. 7 depicts the verification of the produced ssDNA schematized in FIG. 6.

A ssDNA insert containing GAPDH homology arms and an AcGFP1 coding sequence was designed and produced essentially as described above. The insert was configured such that upon insertion into a host genome by homologous recombination mediated by CRISPR/Cas9 targeting the C-terminus of GAPDH the AcGFP1 coding sequence would be in-frame with the GAPDH coding sequence (FIG. 6). Production of sense ssDNA of the described construct was performed essentially as described above and confirmed by agarose-gel electrophoresis (FIG. 7).

Figure 8:
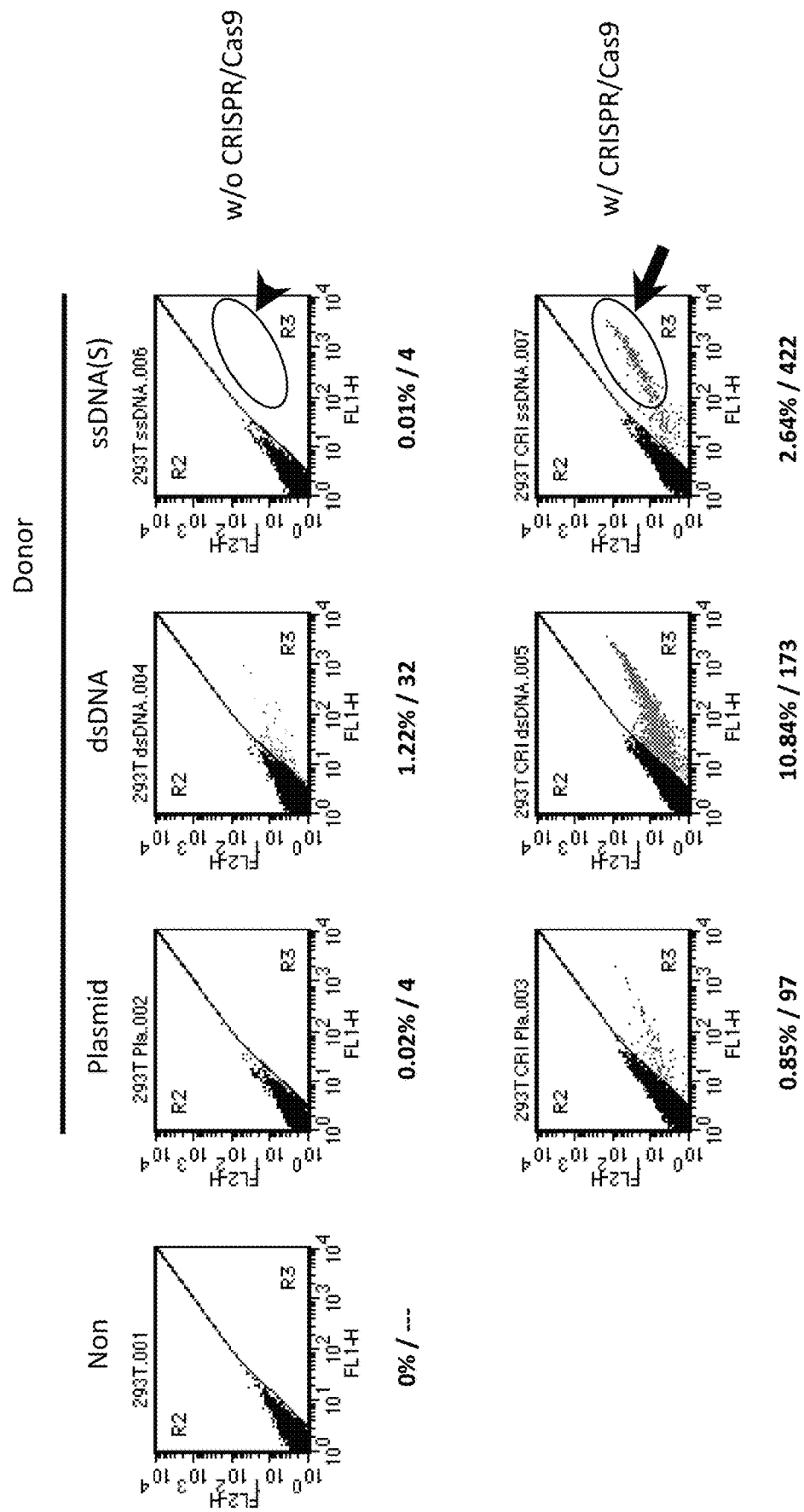
FIG. 8 depicts the successful targeted integration of produced ssDNA using CRISPR/Cas9 homology directed repair according to certain embodiments.

Produced sense ssDNA ("ssDNA(S)") of the GAPDH targeting construct was transfected by electroporation into HEK293T cells in the presence ("w/ CRISPR/Cas9") and in the absence ("w/o CRISPR/Cas9") of CRISPR/Cas9 (FIG. 8). Cells were cultured for three days following transfection, at which time cells were detached and integration by homologous recombination was assessed by fluorescence activated cell sorting (FACS) to detect AcGFP1 expression. Non-transfected cells ("Non"), linear dsDNA donor ("ds-DNA") transfected cells and circular plasmid containing the dsDNA sequence ("plasmid") transfected cells were used as controls.

As depicted in FIG. 8, FACS analysis showed that homologous recombination using a ssDNA donor resulted in cells with high green fluorescent signal generated by the GAPDH-AcGFP1 fusion protein, consistent with the high expression level of endogenous GAPDH. Specifically, when ssDNA donor was used with CRISPR/Cas9, cells with high green fluorescence were generated as detected by FACS (see FIG. 8 and compare the ovals identified in the "ssDNA(S)" column showing the appearance of highly fluorescent cells when CRISPR/cas9 was used (arrow) as compared to control (arrowhead)). While the frequency of recombination was moderate, background integration in the absence of genome targeting endonuclease ("w/o CRISPR/Cas9") was lowest using the ssDNA donor, particularly as compared to the over 1% background integration seen using dsDNA donor. The results of the FACS analysis are presented below in Table 1.

TABLE 1

| | Transfection | Mean Fluorescence Intensity (MFI) | Frequency of Recombination |
|---|---|---|---|
| CRISPR/Cas9 Absent | None | — | 0% |
| | Plasmid | 4 | 0.02% |
| | dsDNA | 32 | 1.22% |
| | ssDNA | 4 | 0.01% |
| CRISPR/Cas9 Present | Plasmid | 97.43 | 0.85% |
| | dsDNA | 173.27 | 10.84% |
| | ssDNA | 421.78 | 2.64% |

Figure 9:
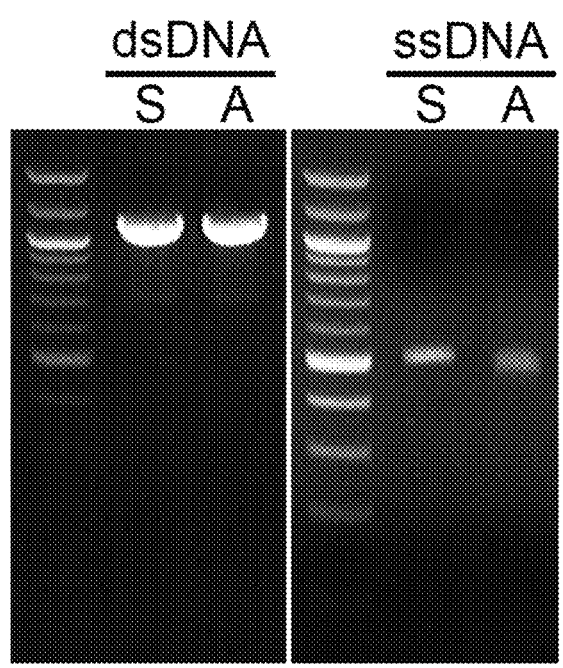
FIG. 9 depicts the verification of the produced sense and antisense ssDNAs used in the homology directed repair of FIG. 10.

The effect of using a sense ssDNA versus an antisense ssDNA was also investigated. Sense-strand ssDNA ("ssDNA(S)") and an antisense-strand ssDNA ("ssDNA(A)") of the GAPDH/AcGFP1 construct were prepared as described above and the ssDNA fragments were confirmed by agarose gel electrophoresis (FIG. 9).

Figure 10:
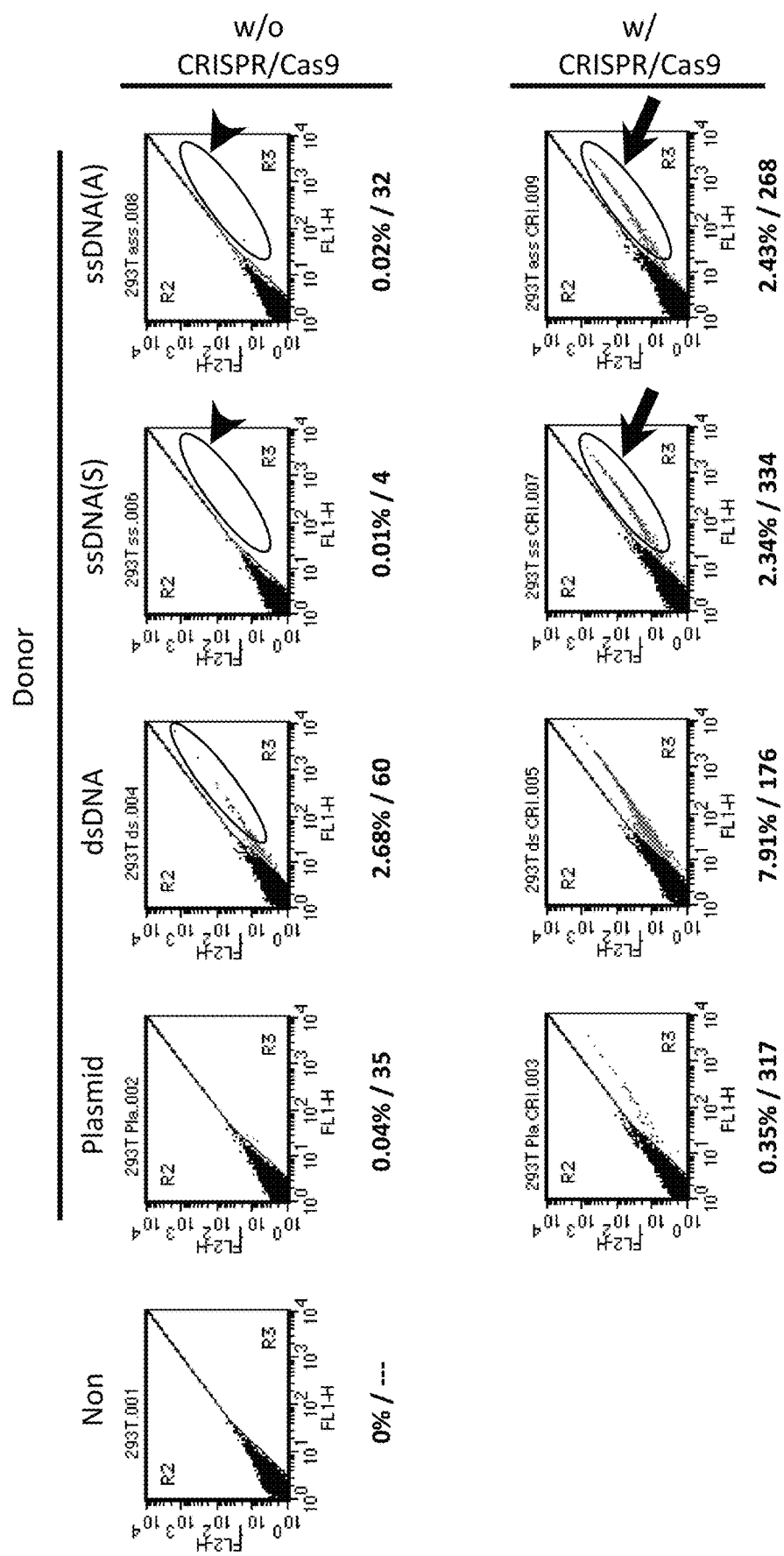
FIG. 10 depicts the successful targeted integration of produced sense and antisense ssDNA using CRISPR/Cas9 homology directed repair according to certain embodiments

The sense and antisense ssDNAs were independently transfected into HEK293T cells in the presence ("w/ CRISPR/Cas9") and in the absence ("w/o CRISPR/Cas9") of CRISPR/Cas9 (FIG. 10). Cells were cultured and then detached and integration by homologous recombination was assessed by FACS to detect AcGFP1 expression. Non-transfected cells ("Non"), linear dsDNA donor ("dsDNA") transfected cells and circular plasmid containing the dsDNA sequence ("plasmid") transfected cells were used as controls.

When ssDNA sense (ssDNA(S)) or ssDNA antisense (ssDNA(A)) donors were used with CRISPR/Cas9, cells with high green fluorescence were generated as detected by FACS (see FIG. 10 and particularly the ovals identified in the "ssDNA(S)" and "ssDNA(A)"columns showing the appearance of highly fluorescent cells when CRISPR/cas9 was used (arrows) as compared to controls (arrowheads)). The sense and antisense ssDNA constructs displayed comparable MFI and frequency of integration. In addition, both the sense and antisense ssDNA constructs showed the lowest amount of background fluorescence when CRISPR/Cas9 was absent (see ovals identified by arrowheads), particularly as compared to the linear dsDNA construct which resulted in over 2% background integration (see oval in the "dsDNA" column). The results of the FACS analysis are presented below in Table 2.

TABLE 2

| | Transfection | Mean Fluorescence Intensity (MFI) | Frequency of Recombination |
|---|---|---|---|
| CRISPR/Cas9 Absent | None | — | 0% |
| | Plasmid | 35 | 0.04% |
| | dsDNA | 60 | 2.68% |
| | ssDNA(S) | 4 | 0.01% |
| | ssDNA(A) | 32 | 0.02% |
| CRISPR/Cas9 Present | Plasmid | 317 | 0.35% |
| | dsDNA | 176 | 7.91% |
| | ssDNA(S) | 334 | 2.34% |
| | ssDNA(A) | 268 | 2.43% |

Example 3

Background Expression in Promoter Containing Inserts

Figure 11:
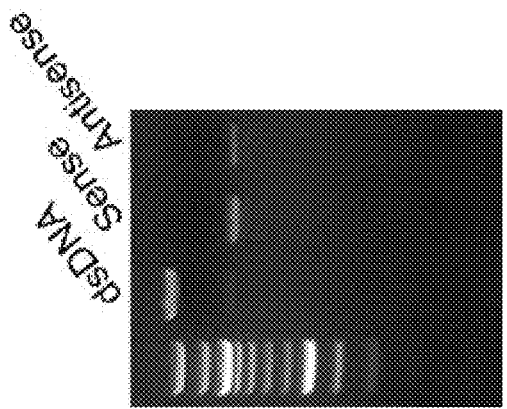
FIG. 11 depicts the verification of the produced sense and antisense ssDNAs used in the transfection of FIG. 12.
Figure 12:
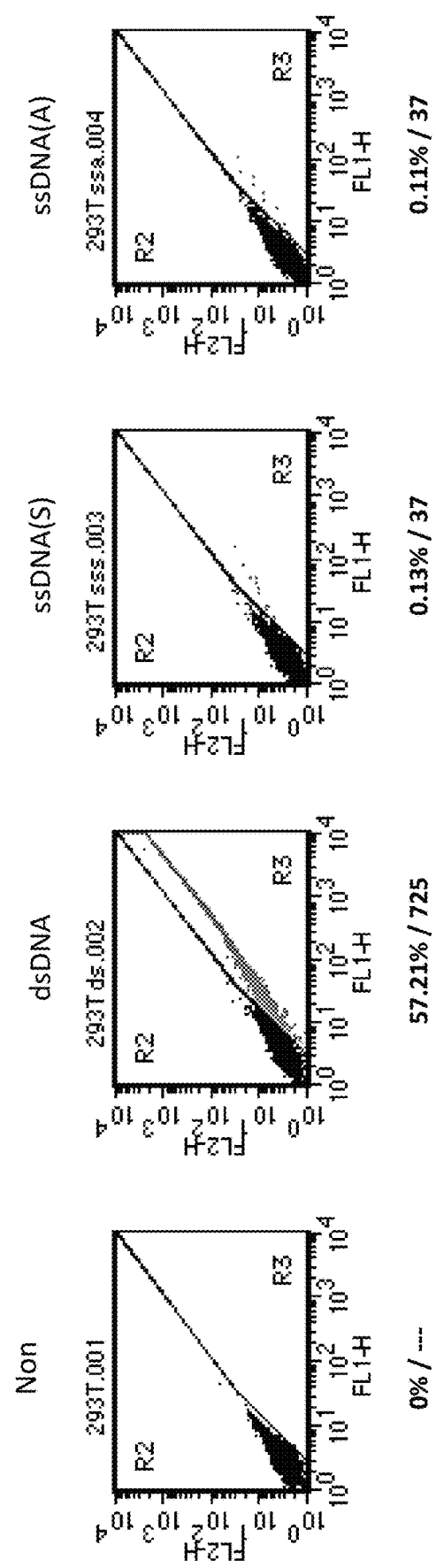
FIG. 12 depicts the relative lack of background signal and integration of both sense and antisense donor ssDNA as compared to dsDNA donor.

The relative background expression of double-stranded vs. single-stranded DNA inserts that contain a functional promoter was investigated. A dsDNA construct was designed and generated that contains a strong cytomegalovirus (CMV) promoter driving sequence encoding AcGFP1. The corresponding sense ssDNA and antisense ssDNA constructs were generated as described above, and their successful generation was confirmed by agarose gel electrophoresis (FIG. 11). The dsDNA, sense ssDNA and antisense ssDNA constructs were independently transfected into HEK293T cells and, after 24 hours of culture, the cells were analyzed for AcGFP1 expression by FACS.

When transfection was performed with the control dsDNA construct strong fluorescence signal was detected from transfected cells (57.21% frequency of positive cells with 725.41 MFI) demonstrating that the construct is functional, expressing AcGFP1 from the CMV promoter. However, expression of AcGFP1 was nearly absent in the cells transfected with sense ssDNA (0.13% frequency of positive cells with 37.48 MFI) or antisense ssDNA (0.11% frequency of positive cells with 37.11 MFI) constructs.

This example demonstrates that, even in constructs containing a functional promoter sequence, neither sense nor antisense ssDNA constructs drive expression of a reporter gene whereas dsDNA constructs, even introduced without an endonuclease, do effectively drive reporter expression. Accordingly, the use of generated ssDNA in genome modification studies presents less danger of spurious expression from introduced constructs as compared to dsDNA, thus demonstrating, e.g., the applicability of ssDNA for use in screening application where low background and the absence of false-positive signal are desirable.

Example 4

Generation of ssDNA of Varied Length

Figure 13:
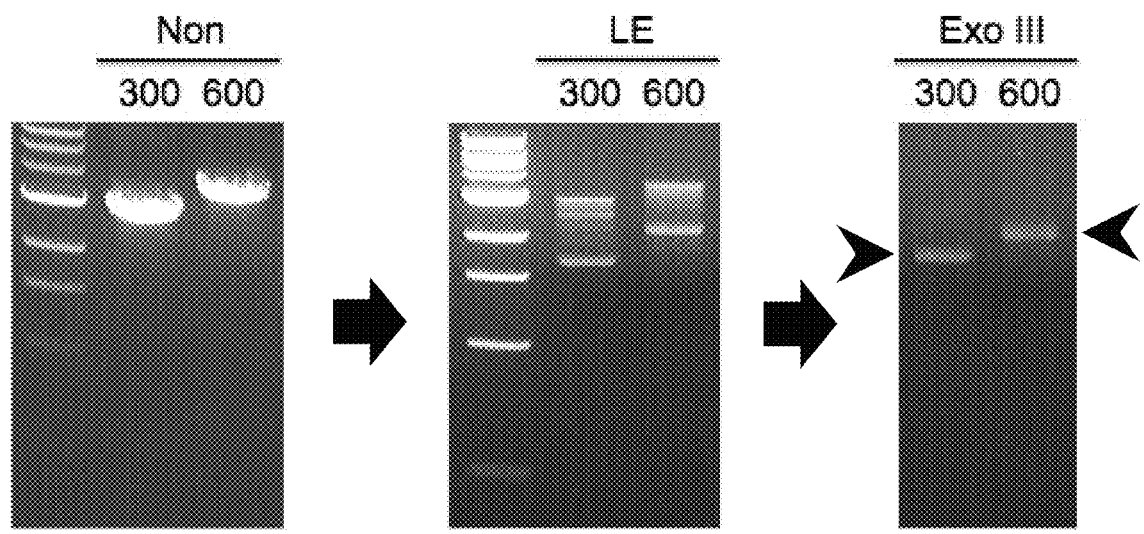
FIG. 13 demonstrates the successful generation of AAVS1/EF1α-AcGFP1 ssDNA from the various constructs having homology arms of different lengths and overall different lengths.
Figure 14:
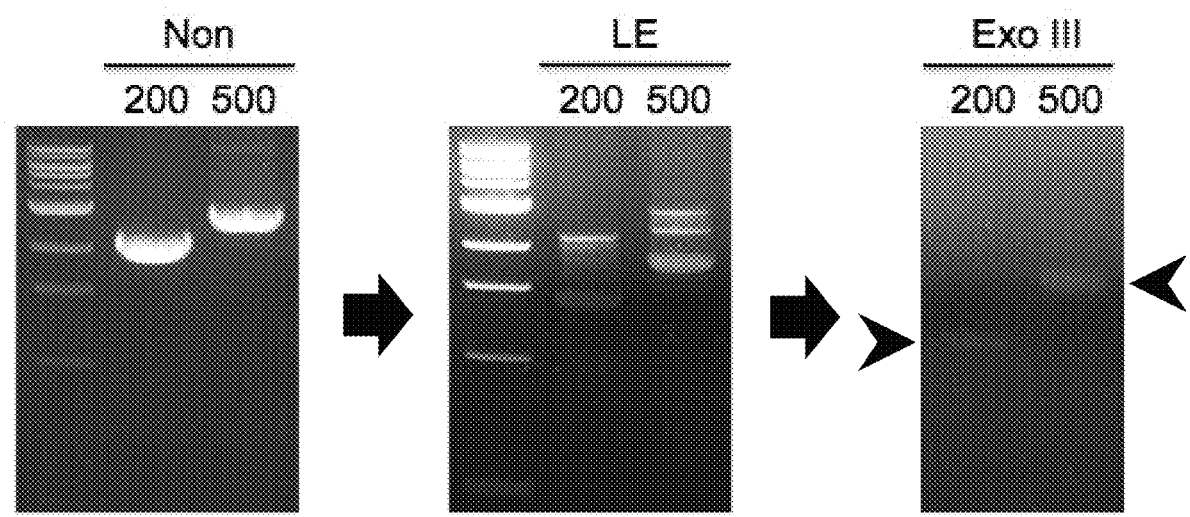
FIG. 14 demonstrates the successful generation of AAVS1/CMV-mCherry ssDNA from the various constructs having homology arms of different lengths and overall different lengths.

The ability to generate ssDNA constructs of varied length and varied sequence was investigated. Constructs targeting the adeno-associated virus integration site 1 (AAVS1) and containing either an elongation factor 1 alpha (EF1α) promoter driving AcGFP1 or a CMV promoter driving mCherry were designed. The length of the AAVS1 homology arms was varied in length from 200 bp to 600 bp. In particular, AAVS1/EF1α-AcGFP1 constructs having 300 bp or 600 bp homology arms were developed as were AAVS1/CMV-mCherry constructs having 200 bp or 500 bp homology arms. ssDNA was generated from the dsDNA constructs essentially as described above. The successful generation of AAVS1/EF1α-AcGFP1 ssDNA and AAVS1/CMV-mCherry ssDNA from the various constructs was confirmed by agarose gel electrophoresis (FIG. 13 and FIG. 14, respectively). FIG. 13 and FIG. 14 provide images of the untreated ("Non") constructs, the constructs following lambda exonuclease ("LE") treatment, and the constructs following exonuclease III ("Exo III") treatment performed following lambda exonuclease treatment. Cleanly produced ssDNA of the various sizes and sequences can be seen in each case following Exo III digestion (arrowheads). In some instances, ssDNA can be inefficiently generated as a result of primer positions. In such instances, primer position can be varied in order to efficiently generate the ssDNA fragment. For example, FIG. 15 shows an exemplary embodiment wherein a ssDNA of 500 bases of the CCR5 region may not be generated, but production can be restored by moving the primers one base upstream or downstream, as shown by the generation of 499 base fragments and 501 base fragments.

This example demonstrates that ssDNA can be successfully generated from constructs of greatly varying total size and sequence using selective degradation of one strand of a dsDNA molecule as described herein. Accordingly, the described methods are widely applicable regardless of construct overall length, which may vary due to the differences in construct configuration including e.g., promoters, coding sequences, homology arms, etc.

Example 5

Removal of Undesired RNA from Total RNA Samples Using ssDNA Specific to the Undesired RNA Species Protein-coding mRNA constitutes only a small portion of the total RNA extracted from growing mammalian cells whereas often undesired RNA species, including ribosomal RNA (rRNA) which constitutes the majority of total RNA (>80%) and transfer RNA (tRNA) which comprises~15%, are much more highly represented (see e.g., Lodish H, et al. Molecular Cell Biology. 4th ed. New York: W. H. Freeman; 2000). Thus, in many biological applications, including e.g., reverse transcription (RT) based cloning and many RNA sequencing methodologies, reducing the amount of undesired RNA species present in a sample at an early stage is desirable.

Sequence specific hybridization of ssDNA to undesired RNA species allows for the selective reduction/removal of the undesired RNA. A process for eliminating undesired RNA will be described specifically for rRNA; however, although not specifically set forth below, similar methodologies may be readily applied to the reduction/removal of any undesired RNA species, including e.g., tRNA, mitochondrial RNA, etc.

A sample of total RNA is prepared from cultured mammalian cells or a mammalian tissue sample according to established protocols. Mammalian rRNA is cloned from the total RNA sample by RT-PCR using either random hexamer primers or primers specifically directed to rRNA. DsDNA representing the rRNA sequences (i.e., ribosomal dsDNA) is produced. Strand-selective degradation is employed to generate, from the ribosomal dsDNA, ribosomal antisense ssDNA that specifically hybridizes to rRNA. As described in more detail below, generated ribosomal antisense ssDNA may be employed in enzyme mediated digestion of the undesired rRNA. Alternatively, also as described in more detail below, ribosomal antisense ssDNA may be generated to include a biotin-label, including e.g., where biotin-labeled nucleotides are incorporated during ribosomal dsDNA synthesis, where the ribosomal dsDNA or ribosomal ssDNA is biotin-labeled by chemical attachment of a biotin moiety, etc., and the strong binding of the biotin label to streptavidin may be employed to remove the unwanted rRNA from the sample.

In one approach, to amplify the ribosomal dsDNA 5'-phosphorylated sense-strand, ribosome specific primers, along with corresponding non-phosphorylated reverse primers, are used. By this process ribosomal dsDNA having a single 5'-phosphorylated sense strand is generated. Next, lambda exonuclease (LE) and appropriate buffer are added to the ribosomal dsDNA and the reaction is incubated at 37° C. to initiate 5'-phosphate selective strand degradation. Following the initiation of LE digestion, exonuclease III (ExoIII) and ExoIII buffer are added to the reaction and the reaction is further incubated at 37° C. Digestion of the 5'-phosphorylated strands of the ribosomal dsDNA is allowed to go to completion, leaving ssDNA having ribosomal antisense sequence, now termed ribosomal antisense ssDNA.

For use in reducing the amount of rRNA in total RNA samples, the produced ribosomal antisense ssDNA may be used directly in its "full-length" form or may be fragmented into shorter ssDNA segments as desired. Any convenient method of fragmentation may be employed including but not limited to e.g., those appropriate methods described in Knierim et al. (2011) PLoS One 6(11): e28240; the disclosure of which is incorporated herein by reference.

To reduce the amount of mammalian rRNA, a total RNA sample is combined with an aliquot of the produced ribosomal antisense ssDNA and an appropriate hybridization buffer. The reaction is incubated in a thermocycler at 95° C. for 2 min. and then cooled (e.g., at about −0.1° C. per sec.) to 25° C. to allow the ribosomal antisense ssDNA to hybridize with rRNA thus forming ssDNA-RNA hybrids.

In one approach, RNase H and RNase H buffer are added to the reaction to digest the ssDNA-rRNA hybrids during an incubation at 37° C. for about 30 min. Following RNase H digestion, to digest unbound DNA remaining in the reaction, DNase I is added to the reaction and the reaction is incubated at 37° C. for an additional 15 min.

In another approach, where the produced ribosomal antisense ssDNA has been modified to include attached biotin moieties, a total RNA sample is combined with an aliquot of the produced the biotin-labeled ribosomal antisense ssDNA and an appropriate hybridization buffer. The reaction is incubated in a thermocycler at 95° C. for 2 min. and then cooled (e.g., at about −0.1° C. per sec.) to 25° C. to allow the biotin-labeled ribosomal antisense ssDNA to hybridize with rRNA thus forming biotin-labeled ssDNA-RNA hybrids. Next, an aliquot of streptavidin-labeled magnetic beads is added to the reaction and the reaction is incubated to allow binding of the streptavidin-labeled magnetic beads to the biotin-labeled ssDNA-RNA hybrids. Following incubation, a magnetic field is applied to the reaction (e.g., by placing a magnet in the reaction, placing the reaction in the vicinity of a magnet, etc.) allowing the magnetic beads with ssDNA-RNA hybrids attached to accumulate in a portion of the reaction vessel, at which point the magnetic beads may be removed from the reaction or the reaction supernatant may be separated from the beads, e.g., by pipetting. By separating the ssDNA-RNA hybrid bound magnetic beads (either by removing the beads or removing the reaction from the beads) the undesired rRNA is separated from the reaction and the remaining RNA is subsequently enriched for non-rRNA species.

Following the above described reduction/removal steps, the desired RNA, which is now enriched for mRNA, can be purified by any convenient method, including but not limited to e.g., magnetic bead isolation/purification, spin column purification, gel purification, lithium chloride precipitation, phenol-chloroform extraction, etc. With or without purification, the desired mRNA enriched sample is suitable for downstream applications including RT-PCR based cloning, sequencing, and the like. In some instances, e.g., depending on the particular downstream application, the desired RNA may be used directly including e.g., where the desired RNA is used directly for next generation sequencing (NGS) library preparation.

Example 6

Figure 16:
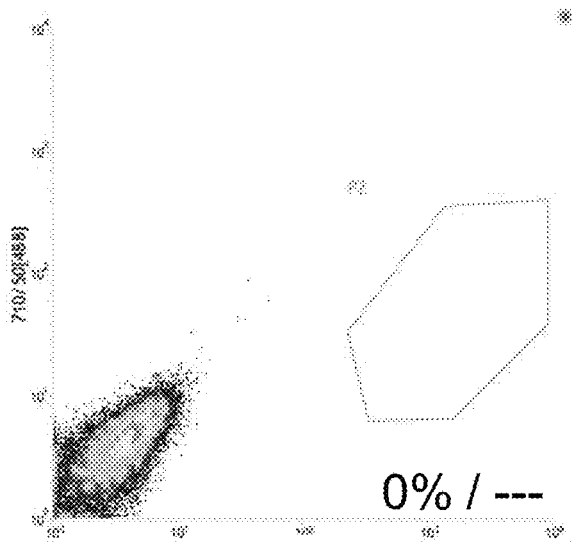
FIG. 16 depicts the successful targeted integration of ssDNA with 300- or 600-b homology arms using CRISPR/Cas9 homology directed repair.
Figure 16:
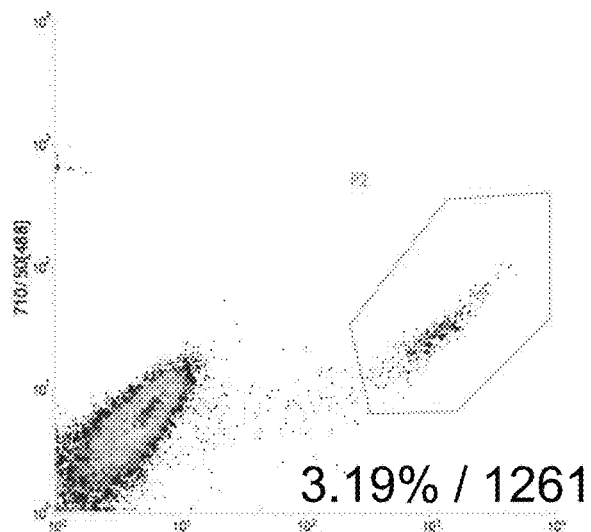
Figure 16:
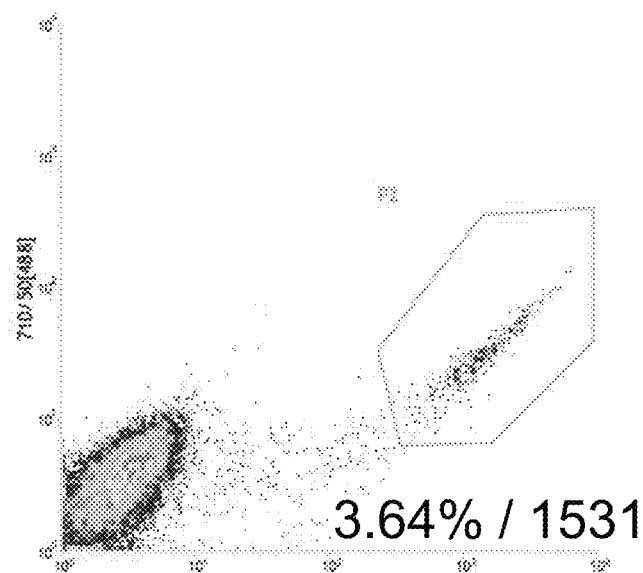

Increased Homologous Recombination Rate with Long Homology Arms ssDNA of Ac-GFP driven by the EF1alpha promoter was generated with homology arms to either GAPDH or AAVS1. Homology arms to AAVS1 were either 300 bases or 600 bases. These ssDNA were electroporated into human inducible pluripotent stem cells (hiPSCs) along with CRISPR/Cas9 Ribonucleo protein (RNP) complex targeted to the AAVS1 site. Expression of AcGFP was analyzed by FACS on day 9 (FIG. 16). By flow cytometry analysis, 3.19% of the cells electroporated with the ssDNA with 300 base homology arms expressed AcGFP. 3.64% of cells electroporated with the ssDNA having 600 base homology arms were found to be expressing AcGFP. GAPDH-AcGFP transfection was successful, though cells positive for expression of AcGFP disappeared between days 3-9 of the expansion of the hiPSCs (FIG. 16, left).

This example demonstrates that the use of homology arms which are 300 or 600 bases result in sufficient homologous recombination of the ssDNA fragment. Accordingly, homology arm length may be varied to alter the frequency of recombination using the methods herein.

Example 7

Figure 17:
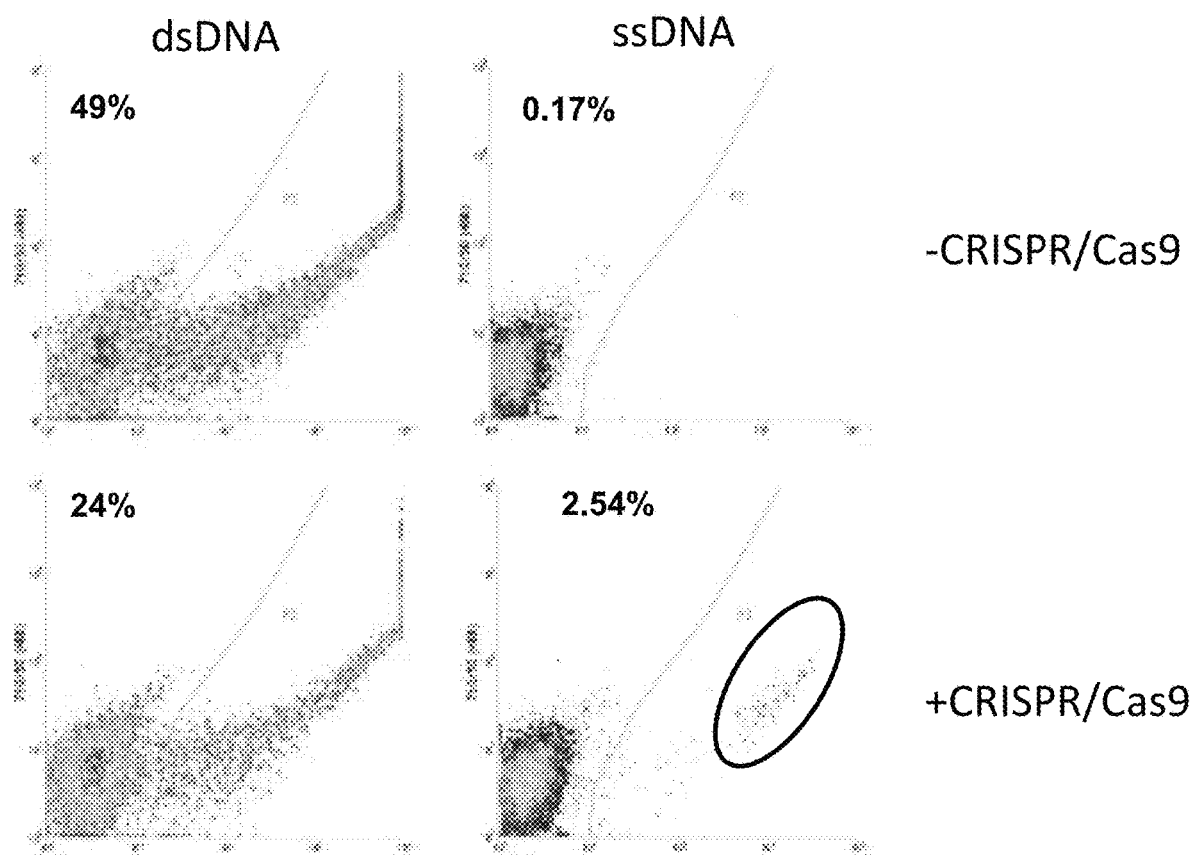
FIG. 17 depicts the decreased background expression of EF1a-AcGFP1 after homology directed repair when ssDNA is used.

Background Expression in Promoter Containing Inserts in Jurkat Cells ssDNA and dsDNA of EF1alpha-AcGFP with homology arms to AAVS1 were produced using the methods described above, and electroporated into Jurkat cells with or without the CRISPR/Cas9 RNP complex targeting the AAVS1 site. Expression of AcGFP was analyzed by FACS analysis after 5 days (FIG. 17). dsDNA transfected cells had very high background expression, with 49% of cells expressing AcGFP without CRISPR/Cas9 present, and 24% of cells expressing AcGFP when CRISPR/Cas9 was co-electroporated with the dsDNA (FIG. 17). Expression of AcGFP from cells electroporated with ssDNA had very low background, with only 0.17% of cells expressing AcGFP without CRISPR/Cas9 present, and 2.54% of cells expressing AcGFP when CRISPR/Cas9 was co-electroporated with the ssDNA (FIG. 17).

This example demonstrates that the background associated with transfection and recombination of dsDNA can be reduced by instead transfecting ssDNA.

Example 8

Bacteriophage-Based Production of Long ssDNA

Linear target double-stranded DNA is prepared by overlapping PCR as described above. The target dsDNA comprises one or more regions of interest, such as one or more genes, gene fragments, or any genetic element. Target dsDNA is flanked by an excision sites and cloning sites. The excision site comprises a first restriction endonuclease binding site. The cloning sites comprise a second and third restriction endonuclease binding site, one on each end of the target dsDNA. The target dsDNA is contacted with a second and third restriction endonuclease which cleave at the second and third restriction endonuclease binding sites, respectively. The M13 phage vector is cleaved in its multiple cloning site with the second and third restriction endonuclease, thereby linearizing the vector and creating sticking ends complementary to the target dsDNA.

The target dsDNA is ligated into the M13 bacteriophage vector. Following ligation of the target dsDNA into the vector, the vector is transformed into host bacteria for propagation with electroporation. The vector comprises one or more antibiotic resistance genes. The bacteria which have been successfully transformed and contain the vector and insert are selected by antibiotic resistance.

The vector is amplified in the *E. coli* host and treated with M13 phage in order to convert the double-stranded vector into a single-stranded vector. Upon lysis, the now single-stranded DNA vector is purified by repeated centrifugation and treatment with sodium chloride and PEG-8000.

The purified single-stranded vector is contacted with oligonucleotides complementary to the excision sites, thereby generating double-stranded excision sites. The double-stranded excision sites are contacted with a first restriction endonuclease with sequence specificity to the double-stranded excision sites. The first restriction endonuclease cleaves the double-stranded excision sites thereby releasing the target ssDNA.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A method of producing a single-stranded DNA (ssDNA), the method comprising:
   (a) generating a double-stranded DNA (dsDNA) comprising a product strand and a complementary strand that differ structurally from one another; and
   (b) selectively degrading the complementary strand based on the structural difference between the product strand and the complementary strand to produce the ssDNA, the selective degradation comprising:
      (i) contacting the dsDNA with a first exonuclease that comprises exonuclease activity that is 5'-phosphate-dependent to generate a partially degraded complementary strand, and
      (ii) contacting the partially degraded complementary strand with a second exonuclease.

2. The method according to claim 1, wherein the dsDNA comprises a 5'-phosphate in the complementary strand, one or more protective base modifications in the product strand or both.

3. The method according to claim 1, wherein the second enzyme is a 3' to 5' exonuclease.

4. The method according to claim 1, wherein the first exonuclease is a lambda exonuclease.

5. The method of claim 4, wherein the 3' to 5' exonuclease is an exonuclease III.

6. The method according to claim 1, wherein the dsDNA is generated by a polymerase chain reaction (PCR).

7. The method according to claim 6, wherein a primer comprising a 5' phosphate is incorporated into the dsDNA during the PCR.

8. The method according to claim 6, wherein one or more protective base modifications are incorporated into the dsDNA during the PCR.

9. The method according to claim 8, wherein a primer comprising at least one of the one or more protective base modifications is incorporated into the dsDNA during the PCR.

10. The method according to claim 1, wherein the dsDNA is generated by a ligation reaction comprising the ligation of two or more dsDNA segments.

11. The method according to claim 10, wherein one of the two or more dsDNA segments comprises a 5' phosphate that, following the ligation reaction, provides a 5' phosphate to the generated complementary strand.

12. The method according to claim 10, wherein at least one of the two or more dsDNA segments comprises a protective base modification.

13. The method according to claim 1, wherein the complementary strand comprises a 5'-phosphate-dependent exonuclease pausing sequence.

14. The method according to claim 1, wherein the ssDNA is greater than 200 bases in length.

15. The method according to claim 14, wherein the ssDNA is greater than 500 bases in length.

16. The method according to claim 15, wherein the ssDNA is greater than 1000 bases in length.

17. The method according to claim 15, wherein the ssDNA ranges from 500 to 10,000 bases in length.

18. The method according to claim 1, wherein the method further comprises testing for the presence of the ssDNA.

19. The method according to claim 1, wherein the dsDNA is blunt-ended at both ends.

20. The method according to claim 1, wherein the first exonuclease and the second exonuclease are present together in a reaction mixture.

21. The method according to claim 20, wherein the second exonuclease is added to a reaction mixture comprising the first exonuclease.

22. A method of modifying genomic DNA, the method comprising:
   (a) producing a ssDNA by a method according to claim 1; and
   (b) contacting a genome with a nuclease and the produced ssDNA under conditions permissive for homology-directed repair in order to generate a modified genome comprising the ssDNA.

23. The method according to claim 22, wherein the contacting step is performed in vitro.

24. The method according to claim 22, wherein the contacting step is performed in vivo.

25. The method according to claim 22, wherein the nuclease is selected from the group consisting of: a Cas9 nuclease, a zinc-finger nuclease and a transcription activator-like effector nuclease.

26. The method according to claim 22, wherein the dsDNA comprises a coding sequence or portion thereof.

27. The method according to claim 26, wherein the coding sequence comprises an exon.

28. The method according to claim 27, wherein the coding sequence comprises a gene or a cDNA.

29. The method according to claim 22, wherein the dsDNA comprises a non-coding sequence or portion thereof.

30. The method according to claim 29, wherein the non-coding sequence comprises a promoter, an enhancer, an intron or a combination thereof.

31. The method according to claim 22, wherein the genome comprises a deleterious mutation and the modified genome comprises a correction of the deleterious mutation.

32. The method according to claim 22, further comprising testing for the presence of the ssDNA in the modified genome.

* * * * *